(12) United States Patent
Zucherman et al.

(10) Patent No.: US 7,670,377 B2
(45) Date of Patent: Mar. 2, 2010

(54) LATERALLY INSERTABLE ARTIFICAL VERTEBRAL DISK REPLACEMENT IMPLANT WITH CURVED SPACER

(75) Inventors: James F. Zucherman, San Francisco, CA (US); Ken Y. Hsu, San Francisco, CA (US); Steven T. Mitchell, Pleasant Hill, CA (US)

(73) Assignee: Kyphon SARL (CH)

( * ) Notice: Subject to any disclaimer, the term of this patent is extended or adjusted under 35 U.S.C. 154(b) by 416 days.

(21) Appl. No.: 10/981,923

(22) Filed: Nov. 5, 2004

(65) Prior Publication Data

US 2005/0283242 A1 Dec. 22, 2005

Related U.S. Application Data

(60) Provisional application No. 60/524,350, filed on Nov. 21, 2003.

(51) Int. Cl.
 *A61F 2/44* (2006.01)
(52) U.S. Cl. .................................. 623/17.15
(58) Field of Classification Search ... 613/17.11–17.16; 606/60–63
 See application file for complete search history.

(56) References Cited

U.S. PATENT DOCUMENTS

| | | |
|---|---|---|
| 572,486 A | 12/1896 | Hom |
| 2,456,806 A | 12/1948 | Wolffe |
| 2,677,369 A | 5/1954 | Knowles |
| 3,320,951 A | 5/1967 | Wittebol |
| 3,426,364 A | 2/1969 | Lumb |
| 3,510,883 A | 5/1970 | Cathcart |
| 3,648,691 A | 3/1972 | Lumb et al. |
| 3,740,769 A | 6/1973 | Haboush |
| 3,867,728 A | 2/1975 | Stubstad et al. |
| 3,875,595 A | 4/1975 | Froning |
| 3,903,549 A | 9/1975 | Deyerle |
| 4,309,777 A | 1/1982 | Patil |
| 4,349,921 A | 9/1982 | Kuntz |
| 4,369,769 A | 1/1983 | Edwards |
| 4,401,112 A | 8/1983 | Rezaian |
| 4,470,158 A | 9/1984 | Pappas et al. |
| 4,479,491 A | 10/1984 | Martin |

(Continued)

FOREIGN PATENT DOCUMENTS

CA 2015507 1/1991

(Continued)

OTHER PUBLICATIONS

International Search Report for PCT/US06/10521 (mailed Nov. 22, 2006).

(Continued)

*Primary Examiner*—Alvin J Stewart

(57) ABSTRACT

An intervertebral disk implant is adapted to be placed between two vertebrae using a lateral insertion method. The implant is characterized by features including a first end plate having a first socket and a second end plate having a second socket with a spacer that is at least partially received in the first socket and the second socket. The implant includes at least one keel that is adapted to be inserted laterally into a vertebral body of the spine. The spacer allows for pivotal or rotational motion and also for twisting motion of the spine once the implant is inserted between vertebrae of a patient.

30 Claims, 15 Drawing Sheets

U.S. PATENT DOCUMENTS

| | | | |
|---|---|---|---|
| 4,499,613 A | 2/1985 | Yarrow | |
| 4,501,269 A | 2/1985 | Bagby | |
| 4,550,450 A | 11/1985 | Kinnett | |
| 4,553,273 A | 11/1985 | Wu | |
| 4,554,914 A | 11/1985 | Kapp et al. | |
| 4,599,084 A | 7/1986 | Nashef | |
| 4,599,086 A | 7/1986 | Doty | |
| 4,622,959 A | 11/1986 | Marcus | |
| 4,636,217 A | 1/1987 | Ogilvie et al. | |
| 4,653,487 A | 3/1987 | Maale | |
| 4,657,550 A | 4/1987 | Daher | |
| 4,681,589 A | 7/1987 | Tronzo | |
| 4,685,447 A | 8/1987 | Iversen et al. | |
| 4,696,290 A | 9/1987 | Steffee | |
| 4,714,469 A | 12/1987 | Kenna | |
| 4,743,256 A | 5/1988 | Brantigan | |
| 4,743,262 A | 5/1988 | Tronzo | |
| 4,759,766 A | 7/1988 | Büttner-Janz et al. | |
| 4,759,769 A | 7/1988 | Hedman et al. | |
| 4,772,287 A | 9/1988 | Ray et al. | |
| 4,790,303 A | 12/1988 | Steffee | |
| 4,805,607 A | 2/1989 | Engelhardt et al. | |
| 4,834,757 A | 5/1989 | Brantigan | |
| 4,863,477 A | 9/1989 | Monson | |
| 4,874,389 A | 10/1989 | Downey | |
| 4,875,474 A | 10/1989 | Border | |
| 4,878,915 A | 11/1989 | Brantigan | |
| 4,892,545 A | 1/1990 | Day et al. | |
| 4,904,260 A | 2/1990 | Ray et al. | |
| 4,904,261 A | 2/1990 | Dove et al. | |
| 4,911,718 A | 3/1990 | Lee et al. | |
| 4,932,969 A | 6/1990 | Frey et al. | |
| 4,932,975 A | 6/1990 | Main et al. | |
| 4,936,363 A | 6/1990 | Schuster et al. | |
| 4,936,848 A | 6/1990 | Bagby | |
| 4,946,378 A | 8/1990 | Hirayama et al. | |
| 4,961,740 A | 10/1990 | Ray et al. | |
| 4,969,888 A | 11/1990 | Scholten et al. | |
| 4,997,432 A | 3/1991 | Keller | |
| 5,002,576 A | 3/1991 | Fuhrmann et al. | |
| 5,004,476 A | 4/1991 | Cook | |
| 5,011,484 A | 4/1991 | Breard | |
| 5,015,247 A | 5/1991 | Michelson | |
| 5,026,373 A | 6/1991 | Ray et al. | |
| 5,035,716 A | 7/1991 | Downey | |
| 5,037,438 A | 8/1991 | Davidson | |
| 5,047,055 A | 9/1991 | Bao et al. | |
| 5,055,104 A | 10/1991 | Ray | |
| 5,059,193 A | 10/1991 | Kuslich | |
| 5,059,194 A | 10/1991 | Michelson | |
| 5,062,850 A | 11/1991 | MacMillan et al. | |
| 5,071,437 A | 12/1991 | Steffee | |
| 5,108,438 A | 4/1992 | Stone | |
| 5,108,442 A | 4/1992 | Smith | |
| 5,122,130 A | 6/1992 | Keller | |
| 5,123,926 A | 6/1992 | Pisharodi | |
| 5,167,662 A | 12/1992 | Hayes et al. | |
| 5,171,280 A | 12/1992 | Baumgartner | |
| 5,171,281 A | 12/1992 | Parsons et al. | |
| 5,180,381 A | 1/1993 | Aust et al. | |
| 5,192,326 A | 3/1993 | Bao et al. | |
| 5,192,327 A | 3/1993 | Brantigan | |
| 5,246,458 A | 9/1993 | Graham | |
| 5,258,031 A | 11/1993 | Salib et al. | |
| 5,258,043 A | 11/1993 | Stone | |
| 5,263,953 A | 11/1993 | Bagby | |
| 5,271,737 A | 12/1993 | Baldwin et al. | |
| 5,282,868 A | 2/1994 | Bahler | |
| 5,290,312 A | 3/1994 | Kojimoto et al. | |
| 5,306,307 A | 4/1994 | Senter | |
| 5,306,308 A | 4/1994 | Gross et al. | |
| 5,306,309 A | 4/1994 | Wagner et al. | |
| 5,313,962 A | 5/1994 | Obenchain | |
| 5,314,477 A * | 5/1994 | Marnay | 623/17.15 |
| 5,314,478 A | 5/1994 | Oka et al. | |
| 5,320,644 A | 6/1994 | Baumgartner | |
| 5,336,223 A | 8/1994 | Rogers | |
| 5,344,458 A | 9/1994 | Bonutti | |
| 5,350,397 A | 9/1994 | Palermo et al. | |
| 5,352,225 A | 10/1994 | Yuan et al. | |
| 5,354,302 A | 10/1994 | Ko | |
| 5,360,430 A | 11/1994 | Lin | |
| 5,366,508 A | 11/1994 | Brekke | |
| 5,370,693 A | 12/1994 | Kelman et al. | |
| 5,370,697 A | 12/1994 | Baumgartner | |
| 5,375,823 A | 12/1994 | Navas | |
| 5,383,884 A | 1/1995 | Summers | |
| 5,390,683 A | 2/1995 | Pisharodi | |
| 5,395,317 A | 3/1995 | Kambin | |
| 5,395,372 A | 3/1995 | Holt et al. | |
| 5,397,364 A | 3/1995 | Kozak et al. | |
| 5,401,269 A * | 3/1995 | Buttner-Janz et al. | 623/17.15 |
| 5,415,704 A | 5/1995 | Davidson | |
| 5,423,816 A | 6/1995 | Lin | |
| 5,423,817 A | 6/1995 | Lin | |
| 5,425,772 A | 6/1995 | Brantigan | |
| 5,425,773 A | 6/1995 | Boyd et al. | |
| 5,425,777 A | 6/1995 | Sarkisian et al. | |
| 5,431,658 A | 7/1995 | Moskovich | |
| 5,439,464 A | 8/1995 | Shapiro | |
| 5,443,514 A | 8/1995 | Steffee | |
| 5,443,515 A | 8/1995 | Cohen et al. | |
| 5,445,639 A | 8/1995 | Kuslich et al. | |
| 5,454,812 A | 10/1995 | Lin | |
| 5,456,722 A | 10/1995 | McLeod et al. | |
| 5,458,638 A | 10/1995 | Kuslich et al. | |
| 5,458,641 A | 10/1995 | Ramirez Jimenez | |
| 5,458,642 A | 10/1995 | Beer et al. | |
| 5,458,643 A | 10/1995 | Oka et al. | |
| 5,480,401 A | 1/1996 | Navas | |
| 5,480,442 A | 1/1996 | Bertagnoli | |
| 5,484,437 A | 1/1996 | Michelson | |
| 5,489,307 A | 2/1996 | Kuslich et al. | |
| 5,489,308 A | 2/1996 | Kuslich et al. | |
| 5,496,318 A | 3/1996 | Howland et al. | |
| 5,505,732 A | 4/1996 | Michelson | |
| 5,507,816 A | 4/1996 | Bullivant | |
| 5,509,934 A | 4/1996 | Cohen | |
| 5,514,180 A | 5/1996 | Heggeness et al. | |
| 5,522,899 A | 6/1996 | Michelson | |
| 5,527,312 A | 6/1996 | Ray | |
| 5,531,793 A | 7/1996 | Kelman et al. | |
| 5,534,023 A | 7/1996 | Henley | |
| 5,534,028 A | 7/1996 | Bao et al. | |
| 5,534,029 A | 7/1996 | Shima | |
| 5,534,030 A | 7/1996 | Navarro et al. | |
| 5,534,031 A | 7/1996 | Matsuzaki et al. | |
| 5,540,689 A | 7/1996 | Sanders et al. | |
| 5,545,229 A | 8/1996 | Parsons et al. | |
| 5,549,679 A | 8/1996 | Kuslich | |
| 5,554,191 A | 9/1996 | Lahille et al. | |
| 5,556,431 A | 9/1996 | Büttner-Janz | |
| 5,562,736 A | 10/1996 | Ray et al. | |
| 5,562,738 A | 10/1996 | Boyd et al. | |
| 5,571,109 A | 11/1996 | Bertagnoli | |
| 5,571,189 A | 11/1996 | Kuslich | |
| 5,571,190 A | 11/1996 | Ulrich et al. | |
| 5,571,192 A | 11/1996 | Schönhöffer | |
| 5,591,235 A | 1/1997 | Kuslich | |
| 5,593,409 A | 1/1997 | Michelson | |
| 5,599,279 A | 2/1997 | Slotman et al. | |
| 5,601,556 A | 2/1997 | Pisharodi | |
| 5,603,713 A | 2/1997 | Aust et al. | |
| 5,609,634 A | 3/1997 | Voydeville | |

| | | | | | |
|---|---|---|---|---|---|
| 5,609,635 A | 3/1997 | Michelson | 5,899,941 A | 5/1999 | Nishijima et al. |
| 5,609,636 A | 3/1997 | Kohrs et al. | 5,906,616 A | 5/1999 | Pavlov et al. |
| 5,609,638 A | 3/1997 | Price et al. | 5,919,235 A | 7/1999 | Husson et al. |
| 5,620,458 A | 4/1997 | Green et al. | 5,928,284 A | 7/1999 | Mehdizadeh |
| 5,645,592 A | 7/1997 | Nicolais et al. | 5,944,754 A | 8/1999 | Vacanti |
| 5,645,596 A | 7/1997 | Kim et al. | 5,945,115 A | 8/1999 | Dunn et al. |
| 5,645,597 A | 7/1997 | Krapiva | 5,961,554 A | 10/1999 | Jamson et al. |
| 5,645,598 A | 7/1997 | Brosnahan, III | 5,964,807 A | 10/1999 | Gan et al. |
| 5,645,599 A | 7/1997 | Samani | 5,976,186 A | 11/1999 | Bao et al. |
| 5,653,761 A | 8/1997 | Pisharodi | 5,980,572 A | 11/1999 | Kim et al. |
| 5,653,762 A | 8/1997 | Pisharodi | 5,984,967 A | 11/1999 | Zdeblick et al. |
| 5,658,335 A | 8/1997 | Allen | 5,989,291 A | 11/1999 | Ralph et al. |
| 5,658,336 A | 8/1997 | Pisharodi | 6,001,130 A | 12/1999 | Bryan et al. |
| 5,658,337 A | 8/1997 | Kohrs et al. | 6,004,573 A | 12/1999 | Rathi et al. |
| 5,658,347 A | 8/1997 | Sarkisian et al. | 6,005,162 A | 12/1999 | Constantz |
| 5,669,909 A | 9/1997 | Zdeblick et al. | 6,010,502 A | 1/2000 | Bagby |
| 5,674,294 A | 10/1997 | Bainville et al. | 6,019,792 A | 2/2000 | Cauthen |
| 5,674,295 A | 10/1997 | Ray et al. | 6,019,793 A | 2/2000 | Perren et al. |
| 5,674,296 A | 10/1997 | Bryan et al. | 6,022,376 A | 2/2000 | Assell et al. |
| 5,676,701 A | 10/1997 | Yuan et al. | 6,039,761 A | 3/2000 | Li et al. |
| 5,676,702 A | 10/1997 | Ratron | 6,039,763 A | 3/2000 | Shelokov |
| 5,683,463 A | 11/1997 | Godefroy et al. | 6,042,582 A | 3/2000 | Ray |
| 5,683,464 A | 11/1997 | Wagner et al. | 6,045,579 A | 4/2000 | Hochshuler et al. |
| 5,683,465 A | 11/1997 | Shinn et al. | 6,045,580 A | 4/2000 | Scarborough et al. |
| 5,693,100 A | 12/1997 | Pisharodi | 6,048,342 A | 4/2000 | Zucherman |
| 5,697,889 A | 12/1997 | Slotman et al. | 6,051,648 A | 4/2000 | Rhee et al. |
| 5,697,977 A | 12/1997 | Pisharodi | 6,068,630 A | 5/2000 | Zucherman |
| 5,700,292 A | 12/1997 | Margulies | 6,074,390 A | 6/2000 | Zucherman et al. |
| 5,702,449 A | 12/1997 | McKay | 6,080,155 A | 6/2000 | Michelson |
| 5,702,450 A | 12/1997 | Bisserie | 6,080,158 A | 6/2000 | Lin |
| 5,702,454 A | 12/1997 | Baumgartner | 6,080,193 A | 6/2000 | Hochshuler et al. |
| 5,702,455 A | 12/1997 | Saggar | 6,086,613 A | 7/2000 | Camino et al. |
| 5,702,469 A | 12/1997 | Whipple et al. | 6,090,112 A | 7/2000 | Zucherman et al. |
| 5,716,415 A | 2/1998 | Steffee | 6,093,205 A | 7/2000 | McLeod et al. |
| 5,716,416 A | 2/1998 | Lin | 6,096,038 A | 8/2000 | Michelson |
| 5,741,253 A | 4/1998 | Michelson | 6,096,080 A | 8/2000 | Nicholson et al. |
| 5,755,732 A | 5/1998 | Green et al. | 6,099,531 A | 8/2000 | Bonutti |
| 5,755,796 A | 5/1998 | Ibo et al. | 6,102,950 A | 8/2000 | Vaccaro |
| 5,755,798 A | 5/1998 | Papavero et al. | 6,102,954 A | 8/2000 | Albrektsson et al. |
| 5,755,811 A | 5/1998 | Tanamal et al. | 6,110,210 A | 8/2000 | Norton et al. |
| 5,766,252 A | 6/1998 | Henry et al. | 6,111,164 A | 8/2000 | Rainey et al. |
| 5,772,661 A | 6/1998 | Michelson | 6,113,637 A | 9/2000 | Gill et al. |
| 5,776,196 A | 7/1998 | Matsuzaki et al. | 6,113,638 A | 9/2000 | Williams et al. |
| 5,776,199 A | 7/1998 | Michelson | 6,113,639 A | 9/2000 | Ray et al. |
| 5,782,830 A | 7/1998 | Farris | 6,120,502 A | 9/2000 | Michelson |
| 5,782,832 A | 7/1998 | Larsen et al. | 6,120,503 A | 9/2000 | Michelson |
| 5,782,919 A | 7/1998 | Zdeblick et al. | 6,123,705 A | 9/2000 | Michelson |
| 5,797,909 A | 8/1998 | Michelson | 6,126,689 A | 10/2000 | Brett |
| 5,800,438 A | 9/1998 | Tuke et al. | 6,127,597 A | 10/2000 | Beyar et al. |
| 5,800,547 A | 9/1998 | Schafer et al. | 6,129,763 A | 10/2000 | Chauvin et al. |
| 5,800,550 A | 9/1998 | Sertich | 6,132,430 A | 10/2000 | Wagner |
| 5,824,093 A | 10/1998 | Ray et al. | 6,132,465 A | 10/2000 | Ray et al. |
| 5,824,094 A | 10/1998 | Serhan et al. | 6,136,001 A | 10/2000 | Michelson |
| 5,827,328 A | 10/1998 | Buttermann | 6,136,031 A | 10/2000 | Middleton |
| 5,836,948 A | 11/1998 | Zucherman et al. | 6,139,579 A | 10/2000 | Steffee et al. |
| 5,860,973 A | 1/1999 | Michelson | 6,146,421 A | 11/2000 | Gordon et al. |
| 5,860,977 A | 1/1999 | Zucherman et al. | 6,146,422 A | 11/2000 | Lawson |
| 5,865,845 A | 2/1999 | Thalgott | 6,149,650 A | 11/2000 | Michelson |
| 5,865,846 A | 2/1999 | Bryan et al. | 6,149,652 A | 11/2000 | Zucherman et al. |
| 5,865,848 A | 2/1999 | Baker | 6,149,686 A | 11/2000 | Kuslich et al. |
| 5,876,404 A | 3/1999 | Zucherman et al. | 6,152,926 A | 11/2000 | Zucherman et al. |
| 5,885,292 A | 3/1999 | Moskovitz et al. | 6,156,038 A | 12/2000 | Zucherman et al. |
| 5,885,299 A | 3/1999 | Winslow et al. | 6,156,067 A | 12/2000 | Bryan et al. |
| 5,888,222 A | 3/1999 | Coates et al. | 6,159,215 A | 12/2000 | Urbahns et al. |
| 5,888,224 A | 3/1999 | Beckers et al. | 6,162,252 A | 12/2000 | Kuras et al. |
| 5,888,226 A | 3/1999 | Rogozinski | 6,165,218 A | 12/2000 | Husson et al. |
| 5,888,227 A | 3/1999 | Cottle ............ 623/17 | 6,176,882 B1 | 1/2001 | Biedermann et al. |
| 5,891,147 A | 4/1999 | Moskovitz et al. | 6,179,874 B1 | 1/2001 | Cauthen |
| 5,893,889 A | 4/1999 | Harrington | 6,183,471 B1 | 2/2001 | Zucherman et al. |
| 5,893,890 A | 4/1999 | Pisharodi | 6,190,387 B1 | 2/2001 | Zucherman et al. |
| 5,895,426 A | 4/1999 | Scarborough et al. | 6,190,414 B1 | 2/2001 | Young et al. |
| 5,895,427 A | 4/1999 | Kuslich et al. | 6,193,757 B1 | 2/2001 | Foley et al. |
| 5,895,428 A | 4/1999 | Berry | 6,206,922 B1 | 3/2001 | Zdeblick et al. |

| | | | | | | |
|---|---|---|---|---|---|---|
| 6,210,412 B1 | 4/2001 | Michelson | | 6,440,168 B1 | 8/2002 | Cauthen |
| 6,224,595 B1 | 5/2001 | Michelson | | 6,440,169 B1 | 8/2002 | Elberg et al. |
| 6,224,607 B1 | 5/2001 | Michelson .................. 606/96 | | 6,443,990 B1 | 9/2002 | Aebi et al. |
| 6,224,631 B1 | 5/2001 | Kohrs | | 6,447,512 B1 | 9/2002 | Landry et al. |
| 6,228,118 B1 | 5/2001 | Gordon | | 6,447,544 B1 | 9/2002 | Michelson |
| 6,231,609 B1 | 5/2001 | Mehdizadeh | | 6,447,547 B1 | 9/2002 | Michelson |
| 6,234,705 B1 | 5/2001 | Troxell | | 6,451,019 B1 | 9/2002 | Zucherman et al. |
| 6,235,030 B1 | 5/2001 | Zucherman et al. | | 6,451,020 B1 | 9/2002 | Zucherman et al. |
| 6,238,397 B1 | 5/2001 | Zucherman et al. | | 6,454,804 B1 | 9/2002 | Ferree |
| 6,241,769 B1 | 6/2001 | Nicholson et al. | | 6,454,807 B1 | 9/2002 | Jackson |
| 6,241,770 B1 | 6/2001 | Michelson | | 6,458,131 B1 | 10/2002 | Ray |
| 6,241,771 B1 | 6/2001 | Gresser et al. | | 6,458,159 B1 | 10/2002 | Thalgott |
| 6,245,072 B1 | 6/2001 | Zdeblick et al. | | 6,461,359 B1 | 10/2002 | Tribus et al. |
| 6,245,108 B1 | 6/2001 | Biscup | | 6,468,310 B1 | 10/2002 | Ralph et al. |
| 6,251,140 B1 | 6/2001 | Marino et al. | | 6,471,724 B2 | 10/2002 | Zdeblick et al. |
| 6,258,125 B1 | 7/2001 | Paul et al. ................. 623/17.11 | | 6,475,219 B1 | 11/2002 | Shelokov |
| 6,261,296 B1 | 7/2001 | Aebi et al. | | 6,478,796 B2 | 11/2002 | Zucherman et al. |
| 6,264,655 B1 | 7/2001 | Pisharodi | | 6,478,822 B1 | 11/2002 | Leroux et al. |
| 6,264,656 B1 | 7/2001 | Michelson | | 6,478,823 B1 | 11/2002 | Michelson |
| 6,264,695 B1 | 7/2001 | Stoy | | 6,482,233 B1 | 11/2002 | Aebi et al. |
| 6,270,498 B1 | 8/2001 | Michelson | | 6,482,235 B1 | 11/2002 | Lambrecht et al. |
| 6,277,149 B1 | 8/2001 | Boyle et al. | | 6,485,517 B1 | 11/2002 | Michelson |
| 6,280,444 B1 | 8/2001 | Zucherman et al. | | 6,488,710 B2 | 12/2002 | Besselink |
| 6,280,475 B1 | 8/2001 | Bao et al. | | 6,500,178 B2 | 12/2002 | Zucherman et al. |
| 6,287,343 B1 | 9/2001 | Kuslich et al. | | 6,500,205 B1 | 12/2002 | Michelson |
| 6,290,724 B1 | 9/2001 | Marino | | 6,503,279 B1 | 1/2003 | Webb et al. |
| 6,296,664 B1 | 10/2001 | Middleton | | 6,514,256 B2 | 2/2003 | Zucherman et al. |
| 6,296,665 B1 | 10/2001 | Strnad et al. | | 6,517,580 B1 * | 2/2003 | Ramadan et al. .......... 623/17.15 |
| 6,302,914 B1 | 10/2001 | Michelson | | 6,520,993 B2 | 2/2003 | James et al. |
| 6,309,421 B1 | 10/2001 | Pisharodi | | 6,520,996 B1 | 2/2003 | Manasas et al. |
| 6,311,562 B1 | 11/2001 | Hanada | | 6,524,312 B2 | 2/2003 | Landry et al. |
| 6,315,795 B1 | 11/2001 | Scarborough et al. | | 6,527,773 B1 | 3/2003 | Lin et al. |
| 6,315,797 B1 | 11/2001 | Middleton | | 6,527,804 B1 | 3/2003 | Gauchet et al. |
| 6,325,827 B1 | 12/2001 | Lin | | 6,527,806 B2 | 3/2003 | Ralph et al. |
| 6,332,882 B1 | 12/2001 | Zucherman et al. | | 6,530,933 B1 | 3/2003 | Yeung et al. |
| 6,332,883 B1 | 12/2001 | Zucherman et al. | | 6,530,955 B2 | 3/2003 | Boyle et al. |
| 6,332,894 B1 | 12/2001 | Stalcup et al. | | 6,540,785 B1 | 4/2003 | Gill et al. |
| 6,342,074 B1 | 1/2002 | Simpson | | 6,547,823 B2 | 4/2003 | Scarborough et al. |
| 6,348,071 B1 | 2/2002 | Steffee et al. | | 6,548,002 B2 | 4/2003 | Gresser et al. |
| 6,350,283 B1 | 2/2002 | Michelson | | 6,554,863 B2 | 4/2003 | Paul et al. |
| 6,364,880 B1 | 4/2002 | Michelson | | 6,558,386 B1 | 5/2003 | Cragg |
| 6,368,350 B1 | 4/2002 | Erickson et al. | | 6,558,387 B2 | 5/2003 | Errico et al. |
| 6,368,351 B1 | 4/2002 | Glenn et al. | | 6,558,390 B2 | 5/2003 | Cragg |
| 6,368,353 B1 | 4/2002 | Arcand | | 6,558,423 B1 | 5/2003 | Michelson |
| 6,371,984 B1 | 4/2002 | Van Dyke et al. | | 6,558,424 B2 | 5/2003 | Thalgott |
| 6,371,988 B1 | 4/2002 | Pafford et al. | | 6,562,073 B2 | 5/2003 | Foley |
| 6,371,989 B1 | 4/2002 | Chauvin et al. | | 6,562,074 B2 | 5/2003 | Gerbec et al. |
| 6,375,681 B1 | 4/2002 | Truscott | | 6,565,570 B2 | 5/2003 | Sterett et al. |
| 6,379,355 B1 | 4/2002 | Zucherman et al. | | 6,569,201 B2 | 5/2003 | Moumene et al. |
| 6,379,385 B1 | 4/2002 | Kalas et al. | | 6,572,653 B1 | 6/2003 | Simonson |
| 6,383,221 B1 | 5/2002 | Scarborough et al. | | 6,572,654 B1 | 6/2003 | Santilli |
| 6,391,030 B1 | 5/2002 | Wagner et al. | | 6,575,982 B1 | 6/2003 | Bonutti |
| 6,391,058 B1 | 5/2002 | Kuslich et al. | | 6,576,016 B1 | 6/2003 | Hochshuler et al. |
| 6,395,030 B1 | 5/2002 | Songer et al. | | 6,576,017 B2 | 6/2003 | Foley et al. |
| 6,395,031 B1 | 5/2002 | Foley et al. | | 6,579,318 B2 | 6/2003 | Varga et al. |
| 6,395,032 B1 | 5/2002 | Gauchet | | 6,579,320 B1 | 6/2003 | Gauchet et al. |
| 6,395,034 B1 | 5/2002 | Suddaby | | 6,579,321 B1 | 6/2003 | Gordon et al. |
| 6,402,785 B1 * | 6/2002 | Zdeblick et al. .......... 623/17.16 | | 6,582,432 B1 | 6/2003 | Michelson |
| 6,409,766 B1 | 6/2002 | Brett | | 6,582,437 B2 | 6/2003 | Dorchak et al. |
| 6,413,278 B1 | 7/2002 | Marchosky | | 6,582,468 B1 | 6/2003 | Gauchet |
| 6,416,551 B1 | 7/2002 | Keller | | 6,607,558 B2 * | 8/2003 | Kuras ...................... 623/17.16 |
| 6,419,676 B1 | 7/2002 | Zucherman et al. | | 6,610,089 B1 | 8/2003 | Liu et al. |
| 6,419,677 B2 | 7/2002 | Zucherman et al. | | 6,626,944 B1 | 9/2003 | Taylor |
| 6,419,704 B1 | 7/2002 | Ferree | | 6,641,614 B1 | 11/2003 | Wagner et al. |
| 6,419,706 B1 | 7/2002 | Graf | | 6,682,562 B2 | 1/2004 | Viart et al. |
| 6,423,063 B1 | 7/2002 | Bonutti | | 6,699,246 B2 | 3/2004 | Zucherman et al. |
| 6,423,095 B1 | 7/2002 | Van Hoeck et al. | | 6,706,068 B2 | 3/2004 | Ferree ...................... 623/17.11 |
| 6,425,920 B1 | 7/2002 | Hamada | | 6,706,070 B1 | 3/2004 | Wagner et al. |
| 6,432,106 B1 | 8/2002 | Fraser | | 6,740,118 B2 | 5/2004 | Eisermann et al. |
| 6,436,098 B1 | 8/2002 | Michelson | | 6,749,635 B1 * | 6/2004 | Bryan ...................... 623/17.16 |
| 6,436,119 B1 | 8/2002 | Erb et al. | | 6,755,841 B2 | 6/2004 | Fraser et al. |
| 6,436,140 B1 | 8/2002 | Liu et al. | | 6,770,095 B2 | 8/2004 | Grinberg |
| 6,436,142 B1 | 8/2002 | Paes et al. | | 6,780,186 B2 | 8/2004 | Errico et al. |

| | | | |
|---|---|---|---|
| 6,793,678 B2 * | 9/2004 | Hawkins | 623/17.15 |
| 6,893,466 B2 | 5/2005 | Trieu | |
| 6,921,403 B2 | 7/2005 | Cragg et al. | |
| 6,936,071 B1 * | 8/2005 | Marnay et al. | 623/17.15 |
| 6,966,929 B2 * | 11/2005 | Mitchell | 623/17.11 |
| 7,048,766 B2 * | 5/2006 | Ferree | 623/17.16 |
| 7,056,344 B2 * | 6/2006 | Huppert et al. | 623/17.16 |
| 7,083,649 B2 * | 8/2006 | Zucherman et al. | 623/17.11 |
| 7,101,375 B2 | 9/2006 | Zucherman et al. | |
| 7,105,024 B2 * | 9/2006 | Richelsoph | 623/17.13 |
| 7,118,580 B1 * | 10/2006 | Beyersdorff et al. | 606/99 |
| 7,179,294 B2 | 2/2007 | Eisermann et al. | |
| 7,326,250 B2 | 2/2008 | Beaurain et al. | |
| 2001/0012938 A1 | 8/2001 | Zucherman | |
| 2002/0128715 A1 | 9/2002 | Bryan et al. | |
| 2003/0191534 A1 * | 10/2003 | Viart et al. | 623/17.15 |
| 2003/0204261 A1 | 10/2003 | Eisermann et al. | |
| 2003/0208273 A1 | 11/2003 | Eisermann et al. | |
| 2003/0233097 A1 | 12/2003 | Ferree | |
| 2004/0002759 A1 | 1/2004 | Ferree | |
| 2004/0073312 A1 | 4/2004 | Eisermann et al. | |
| 2004/0073313 A1 | 4/2004 | Link et al. | |
| 2004/0106998 A1 | 6/2004 | Ferree | |
| 2004/0117022 A1 | 6/2004 | Marnay et al. | |
| 2004/0138750 A1 | 7/2004 | Mitchell | |
| 2004/0143332 A1 * | 7/2004 | Krueger et al. | 623/17.14 |
| 2004/0153157 A1 | 8/2004 | Keller | |
| 2004/0225360 A1 | 11/2004 | Malone | |
| 2004/0225363 A1 | 11/2004 | Richelsoph | |
| 2004/0225365 A1 * | 11/2004 | Eisermann et al. | 623/17.15 |
| 2004/0225366 A1 | 11/2004 | Eisermann et al. | |
| 2004/0230307 A1 | 11/2004 | Eisermann | |
| 2004/0243240 A1 | 12/2004 | Beaurain et al. | |
| 2005/0021145 A1 | 1/2005 | de Villiers et al. | |
| 2005/0043802 A1 | 2/2005 | Eisermann et al. | |
| 2005/0065611 A1 * | 3/2005 | Huppert et al. | 623/17.15 |
| 2005/0102029 A1 | 5/2005 | Blain | |
| 2005/0125065 A1 * | 6/2005 | Zucherman et al. | 623/17.15 |
| 2005/0154462 A1 * | 7/2005 | Zucherman et al. | 623/17.15 |
| 2005/0159818 A1 | 7/2005 | Blain | |
| 2005/0159819 A1 | 7/2005 | McCormack et al. | |
| 2005/0256579 A1 * | 11/2005 | Keller et al. | 623/17.15 |
| 2005/0267581 A1 * | 12/2005 | Marnay et al. | 623/17.14 |
| 2006/0004377 A1 * | 1/2006 | Keller | 606/99 |
| 2006/0036326 A1 | 2/2006 | Baumgartner et al. | |

FOREIGN PATENT DOCUMENTS

| | | | |
|---|---|---|---|
| CH | 624573 A5 | 8/1981 | |
| DE | 2804936 | 2/1979 | |
| DE | 3032353 C2 | 9/1981 | |
| DE | 3113142 | 1/1982 | |
| DE | 4012622 | 7/1991 | |
| EP | 0307241 B1 | 3/1989 | |
| EP | 0322334 | 6/1989 | |
| FR | 2724108 A1 | 2/1994 | |
| FR | 2705227 | 11/1994 | |
| FR | 2707864 | 1/1995 | |
| FR | 2717066 | 9/1995 | |
| FR | 2717068 | 9/1995 | |
| FR | 2718635 A1 | 9/1995 | |
| FR | 2742653 A1 | 12/1995 | |
| FR | 2722088 | 1/1996 | |
| FR | 2722980 | 2/1996 | |
| FR | 2724554 | 3/1996 | |
| FR | 2730156 A1 | 8/1996 | |
| FR | 2780269 A1 | 12/1999 | |
| FR | 2806614 A1 | 9/2001 | |
| GB | 780652 | 8/1957 | |
| JP | 2261446 | 10/1990 | |
| WO | WO 90/00037 | 1/1990 | |
| WO | WO 95/31158 A | 11/1995 | |
| WO | WO 99/26562 | 6/1999 | |
| WO | WO 99/59669 | 11/1999 | |
| WO | WO 00/04851 | 2/2000 | |
| WO | WO 00/13619 | 3/2000 | |
| WO | WO 00/13620 | 3/2000 | |
| WO | WO 00/23015 A1 | 4/2000 | |
| WO | WO 01/01893 A1 | 1/2001 | |
| WO | WO 01/89428 A2 | 11/2001 | |

OTHER PUBLICATIONS

*Ceramic Interspinous Block (CISB) Assisted Anterior Interbody Fusion*, Haruo Tsuji, Norikazu Hirano, Yoshiharu Katoh, Hiroshi Ohsima, Hirokazu Ishihara, Hisao Matsui,and Yohihiko Hayashi, *Journal of Spinal Disorders* vol. 3, No. 1, pp. 77-86, c1990 Raven Press, Ltd., New York.

*Instrumentation and Implants for Spinal Surgery*,J. Dabb, *Diary of the XVIIth Scientific Meeting of the PTO Tr/Pamietnik XVIII Zjazdu Naukowego PTO TR/PZ,WL, Warszawa*, Link America Inc., 1971, 665.

*Spinal Stenosis and Neurogenic Claudication*, Richard W. Porter, MD, FRCS, FRCSE,*SPINE* vol. 21, No. 17, pp. 2046-2052, c1996, Lippincott-Raven Publishers.

*Preliminary Design and Experimental Studies of a Novel Soft Implant for Correcting Sagittal Plan Instability in the Lumbar Spine*, R.J.Minns, BEng, Msc, PhD, DscTech, and W.K. Walsh, FRCS, *SPINE* vol. 22, No. 16, pp. 1819-1827, c1997, Lippincott-Raven Publishers.

Viscoglioski Bro., LLC, Spine Arthoplasty: Market Potential & Technology Update, Spine Industry Analysis Series, Nov. 2001, pp. 1-215.

Jeanette E. Ahrens, PHD, Alexis P. Shelokov, MD, Jeffrey L. Carver, BS, Normal Joint Mobility is Maintained with an Artifical Disc Prothesis, Texas Health Research Institute, Plano, Texas, HCA Columbia Hospital, Plano, Texas, Joint Biomedical Engineering Program, University of Texas Arlington, Link America, Inc., Denville NJ and Waldemar Link, Inc., Hamburg, Germany, 1999.

T. Hoogland, A. D. Steffe, J.D. Black, A.S. Greenwald, Cleveland Clinic Foundation, 24 Annual ORS Dallas, Texas, Feb. 21-23, 1978.

David S. Hungerford, M.D., Kenneth A. Krackow, M.D., Robert V. Kenna, Total Knee Arthoplasty: A Comprehensive Approach, Williams & Williams, Baltimore, MD., 1984, Chapter 5, pp. 71-88.

David S. Hungerford, M.D., and Robert V. Kenna, Preliminary Experience with a Total Knee Prothesis with Porous Coating Used Without Cement, J.B. Lippincott, Co., No. 176, Jun. 1983, pp. 95-107.

Ab Swanson, Gd Swanson, T Powers, Ma Khalil, Bk Maupin, De Mayhew and Sh Moss, The Journal of Bone & Joint Surgery: Unicompartmental and bicompartmental arthroplasty of the knee with a finned metal tibial-plateau implant, vol. 67-A, No. 8, Oct. 1995, pp. 1175-1182, The Journal of Bone & Joint Surgery, Jun. 1994.

The Journal of Bone and Joint Surgery, Sep. 1971, American Volume, vol. 53-A, No. 6, Zimmer, Warsaw, Indiana, U.S.A., Zimmer of Canada, Ltd.

The Journal of Bone and Joint Surgery, Jul. 1970, American Volume, vol. 52-A, No. 5, Zimmer, Warsaw, Indiana, U.S.A., Zimmer of Canada, Ltd.

A.H. Crenshaw, Cambell's Operative Orthopedics, Seventh Edition, vol. Two, The C.V. Mosby Company, copyright, 1987.

* cited by examiner

LATERALLY INSERTABLE ARTIFICAL VERTEBRAL DISK REPLACEMENT IMPLANT WITH CURVED SPACER

CLAIM OF PRIORITY

This application claims priority to U.S. Provisional Patent Application No. 60/524,350, filed Nov. 21, 2003, entitled "ARTIFICIAL VERTEBRAL DISK REPLACEMENT IMPLANT WITH A SPACER AND LATERAL IMPLANT METHOD," which is incorporated herein by reference.

CROSS-REFERENCE TO RELATED APPLICATIONS

This application is related to U.S. Provisional Application No. 60/422,039, filed Oct. 29, 2002, entitled "ARTIFICIAL VERTEBRAL DISK REPLACEMENT IMPLANT WITH TRANSLATING PIVOT POINT AND METHOD," U.S. patent application Ser. No. 10/684,669, filed Oct. 14,2003, entitled "ARTIFICIAL VERTEBRAL DISK REPLACEMENT IMPLANT WITH TRANSLATING PIVOT POINT AND METHOD," U.S. Provisional Application No. 60/422,011, filed Oct. 29, 2002, entitled "TOOLS FOR IMPLANTING AN ARTIFICIAL VERTEBRAL DISK AND METHOD," U.S. patent application Ser. No. 10/685,134, filed Oct. 14,2003, entitled "TOOLS FOR IMPLANTING AN ARTIFICIAL VERTEBRAL DISK AND METHOD," U.S. Provisional Application No. 60/422,022, filed Oct. 29, 2002, entitled "ARTIFICIAL VERTEBRAL DISK REPLACEMENT IMPLANT WITH A SPACER AND METHOD," U.S. patent application Ser. No. 10/685,011, filed Oct. 14, 2003, entitled "ARTIFICIAL VERTEBRAL DISK REPLACEMENT IMPLANT WITH SPACER AND METHOD," and U.S. Provisional Application No. 60/517,973, filed Nov. 6, 2003, entitled "ARTIFICIAL VERTEBRAL DISK REPLACEMENT IMPLANT WITH CROSSBAR SPACER AND LATERAL IMPLANT METHOD," U.S. patent application Ser. No. 10/981,863, filed Nov. 5, 2004, entitled "LATERALLY INSERTABLE ARTIFICIAL VERTEBRAL DISK REPLACEMENT IMPLANT WITH TRANSLATING PIVOT POINT," U.S. patent application Ser. No. 10/981,807, filed Nov. 5, 2004, entitled "METHOD OF LATERALLY INSERTING AN ARTIFICIAL VERTEBRAL DISK REPLACEMENT IMPLANT WITH TRANSLATING PIVOT POINT," U.S. patent application Ser. No. 10/982,638, filed Nov 5, 2004, entitled "LATERALLY INSERTABLE ARTIFICIAL VERTEBRAL DISK REPLACEMENT IMPLANT WITH A CROSSBAR SPACER," U.S. patent application Ser. No. 10/981,952, filed Nov. 5, 2004, entitled "METHOD OF LATERALLY INSERTING ARTIFICIAL VERTEBRAL DISK REPLACEMENT IMPLANT WITH A CROSSBAR SPACER," U.S. patent application Ser. No. 10/981,945, filed Nov. 5, 2004, entitled "METHOD OF LATERALLY INSERTING AN ARTIFICIAL VERTEBRAL DISK REPLACEMENT IMPLANT WITH A SPACER," all of which are incorporated herein by reference.

FIELD OF ART

This field of art of this disclosure is directed to an artificial vertebral disk replacement and method.

BACKGROUND

The spinal column is a biomechanical structure composed primarily of ligaments, muscles, vertebrae and intervertebral disks. The biomechanical functions of the spine include: (1) support of the body, which involves the transfer of the weight and the bending movements of the head, trunk and arms to the pelvis and legs, (2) complex physiological motion between these parts, and (3) protection of the spinal cord and nerve roots.

As the present society ages, it is anticipated that there will be an increase in adverse spinal conditions which are characteristic of aging. For example, with aging comes an increase in spinal stenosis (including, but not limited to, central canal and lateral stenosis), and facet joint degeneration. Spinal stenosis typically results from the thickening of the bones that make up the spinal column and is characterized by a reduction in the available space for the passage of blood vessels and nerves. Facet joint degeneration results from the constant load borne by the facet joints, and the eventual wear that results. Pain associated with both conditions can be relieved by medication and/or surgery.

In addition to spinal stenosis, and facet joint degeneration, the incidence of damage to the intervertebral disks is also common. The primary purpose of the intervertebral disk is to act as a shock absorber. The disk is constructed of an inner gel-like structure, the nucleus pulposus (the nucleus), and an outer rigid structure comprised of collagen fibers, the annulus fibrosus (the annulus). At birth, the disk is 80% water, and then gradually diminishes with time, becoming stiff. With age, disks may degenerate, and bulge, thin, herniate, or ossify. Additionally, damage to disks may occur as a result disease, trauma or injury to the spine.

The damage to disks may call for a range of restorative procedures. If the damage is not extensive, repair may be indicated, while extensive damage may indicate full replacement. Regarding the evolution of restoration of damage to intervertebral disks, rigid fixation procedures resulting in fusion are still the most commonly performed surgical intervention. However, trends suggest a move away from such procedures. Currently, areas evolving to address the shortcomings of fusion for remediation of disk damage include technologies and procedures that preserve or repair the annulus, that replace or repair the nucleus, and that advance implants for total disk replacement. The trend away from fusion is driven both by issues concerning the quality of life for those suffering from damaged intervertebral disks, as well as responsible health care management. These issues drive the desire for procedures that are minimally invasive, can be tolerated by patients of all ages, especially seniors, and can be performed preferably on an out patient basis.

Most recently, there has been an increased interest in total disk replacement technology. A number of artificial disks are beginning to appear in the medical device marketplace. These artificial disks vary greatly in shape, design and functionality. With these devices go tools and methods for insertion between vertebrae thereof.

Accordingly, there is a need in the art for innovation in technologies and methods that advance the art in the area of minimally invasive intervertebral disk replacement. This not only enhances the quality of life for those suffering from the condition, but is responsive to the current needs of health care management.

DETAILED DESCRIPTION

The following description is presented to enable any person skilled in the art to make and use what is disclosed. Various modifications to the embodiments described will be readily apparent to those skilled in the art, and the principles defined herein can be applied to other embodiments and applications without departing from the spirit and scope of what is disclosed and defined by the appended claims. Thus, what is disclosed is not intended to be limited to the embodiments shown, but is to be accorded the widest scope consistent with the principles and features disclosed herein. To the extent necessary to achieve a complete understanding of what is disclosed herein, the specification and drawings of all patents and patent applications cited in this application are incorporated herein by reference.

Figure 1A:
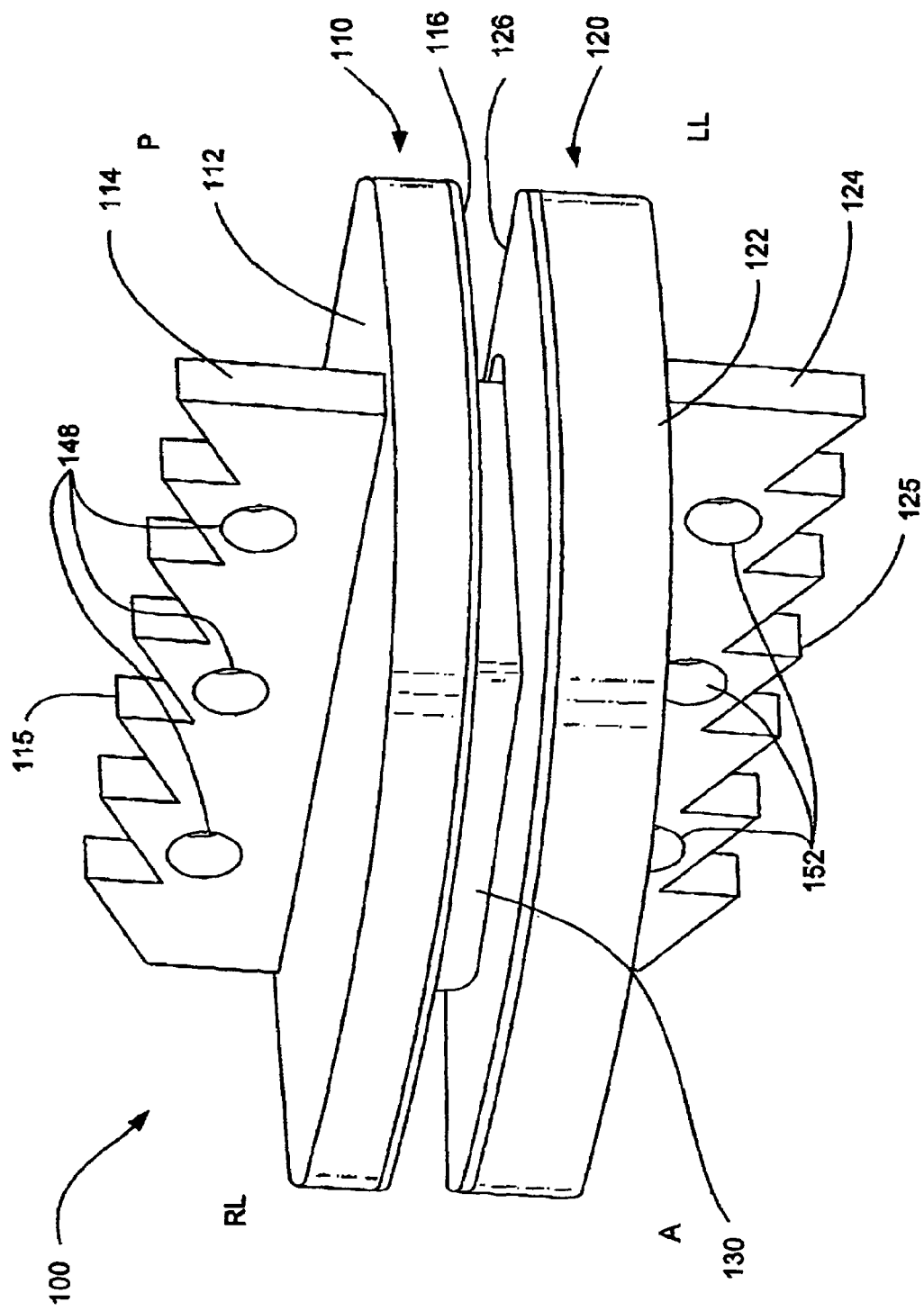
FIG. 1A is a side perspective view of an embodiment of the assembled implant 100.

FIG. 1A shows an embodiment of implant 100. The designations, "A" for anterior, "P" for posterior, "RL" for right lateral, and "LL" for left lateral are given in the drawings for spatial orientation. These designations give the relationship of all faces of implant from the superior perspective; i.e. looking down the axis of the spine. Implant 100 has a first end plate, or upper end plate 110 that is configured to mate with a first vertebra, and a second end plate, or lower end plate 120 that is configured to mate with a second vertebra. A third part 130 that sits between the first end plate 110 and the second end plate 120 is also provided. The third part 130 acts as a spacer between the first end plate 110 and the second end plate 120 and facilitates pivotal or rotational and also twisting movement of the first end plate 110 and the second end plate 120, relative to each other. The third part 130, the spacer, is dimensioned so that it has a curved or convex upper surface and a curved or convex lower surface, as discussed in more detail below.

Figure 1B:
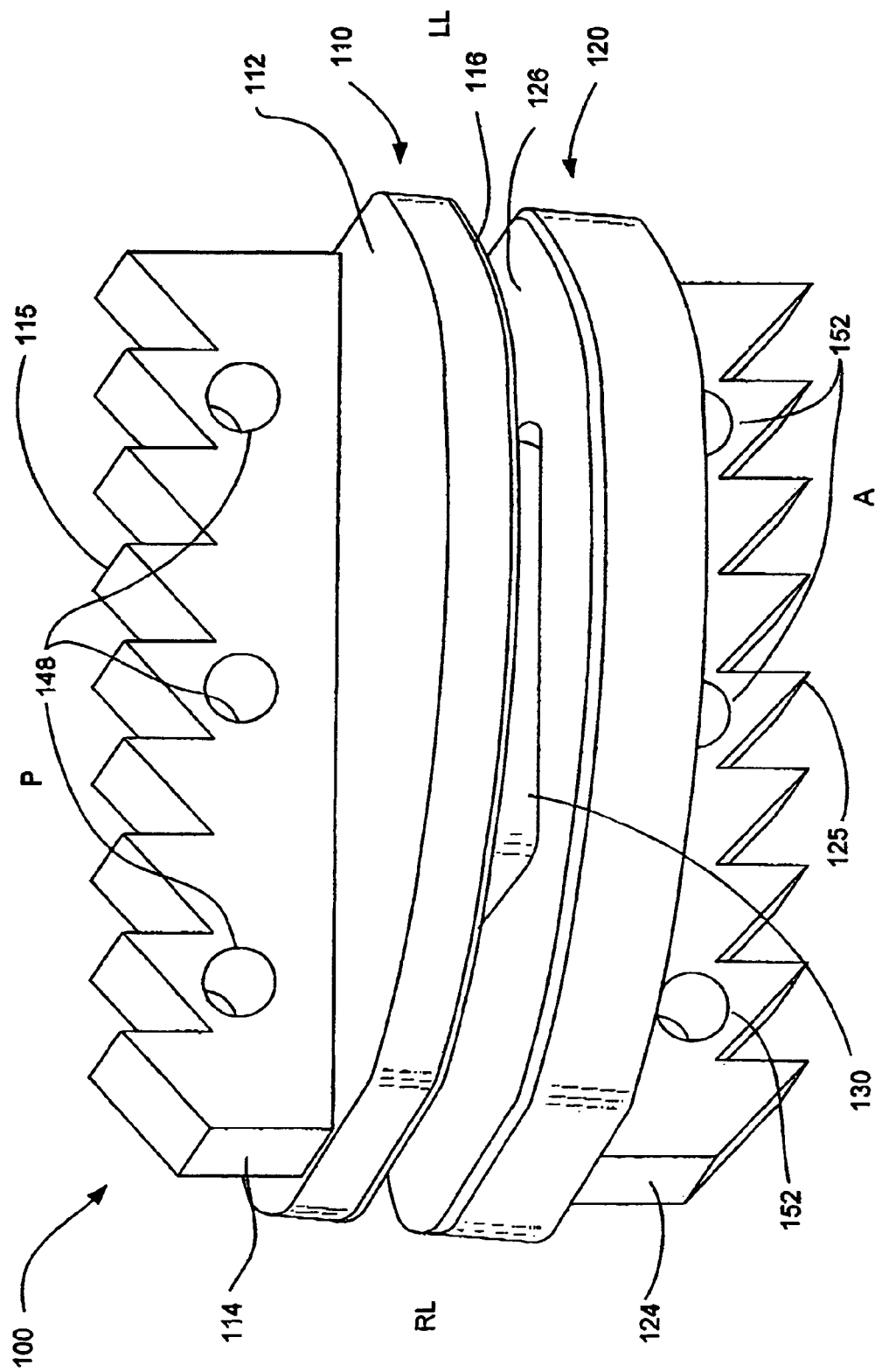
FIG. 1B is an alternative side perspective view of an embodiment of the assembled implant 100.

The upper end plate 110 has a first outer surface 112 from which a first keel 114 extends with a first set of teeth 115. In one embodiment, when implant 100 is inserted between vertebrae, the first keel 114 extends longitudinally across the first outer surface 112, about perpendicular to the sagittal plane of the spine. In another embodiment, the first keel 114 extends longitudinally only partially across the first outer surface 112, about perpendicular to the sagittal plane of the spine. The teeth in the two embodiments with complete or partial extension of the keel across the first outer surface 112 of the upper end plate 110, point towards the left lateral face of implant 100 when the embodiment is meant to be put into a slot in a vertebral body from the left lateral approach to the spine. This orientation is shown in FIG. 1A and FIG. 1B, for example. Alternatively, the teeth 115 point towards the right lateral face of implant 100 when the embodiments are meant to be put into a slot in a vertebral body from the right lateral approach to the spine.

The first outer surface 112 abuts the vertebral body when implant 100 is inserted between vertebrae. The first keel 114 extends into the vertebral body to anchor implant 100 into position, and is perpendicular to the median sagittal plane of the spine, in which extension and flexion occur. The first keel 114 in this orientation offers substantial stability during extension and flexion for implant 100 inserted between the vertebrae of a patient. Additionally, the first keel 114 in this embodiment is aligned with and supports the lateral axis of articulation of implant 100 perpendicular to the sagittal plane of the spine. The first inner surface 116 engages the spacer 130 of implant and opposes the second end plate 120. The first inner surface 116 can form a planar surface that is parallel to the first outer surface 112, or can form a planar surface that is not parallel to the first outer surface 112.

The lower end plate 120 has a second outer surface 122 from which a keel second 124 extends with a second set of teeth 125. In one embodiment, when implant 100 is inserted between vertebrae, the second keel 124 is about perpendicular to the sagittal plane of the spine. As described above for the first upper end plate 110, in one embodiment, the second keel 124 extends longitudinally across the second outer surface 122, while in another embodiment, the second keel 124 extends longitudinally partially across the second outer surface 122. Similarly, the teeth in the two embodiments with complete or partial extension of the keel across the second outer surface 122 of the lower end plate 120 point towards the left lateral face of implant 100 when the embodiment is meant to be put into a slot in a vertebral body from the left lateral approach to the spine. Alternatively, the teeth 125 point towards the right lateral face of implant 100 when the embodiments are meant to be put into a slot in a vertebral body from the right lateral approach to the spine.

The second outer surface 122 abuts the vertebral body when implant 100 is inserted. The second keel 124 extends into the vertebral body to anchor implant 100 into position, and is perpendicular to the median sagittal plane of the spine, in which extension and flexion occur. The second keel 124 in this orientation offers substantial stability during extension and flexion for implant 100 inserted between the vertebrae of a patient. Additionally, the second keel 124 in this embodiment is aligned with and supports the lateral axis of articulation of implant 100 perpendicular to the sagittal plane of the spine. The second inner surface 126, engages the spacer 130 of implant and opposes the first end plate 110. The second inner surface 126 can form a planar surface that is parallel to the second outer surface 122, or can form a planar surface that is not parallel to the second outer surface 122.

The lateral orientation of the first keel 114 and the second keel 124 allow the implant 100 to be inserted into the spine using an advantageous lateral approach as opposed to an anterior or posterior approach. In comparison to a posterior insertion approach in which the spinal nerves can be substantially disturbed, the spinal nerves are bypassed and relatively undisturbed when the implant 100 is inserted laterally between the vertebral bodies from the side of the spine. Although an anterior insertion approach has its benefits, the lateral insertion approach can allow the present implant 100, and associated implantation tools, to be inserted into the spine with less disturbance of the patient's internal organs. This can translate into less time and risk associated with preparing the spine for insertion as well as inserting the implant itself into the spine. Further, the laterally oriented first and second keels 114, 124 offer substantial stability to the vertebral bodies during extension, flexion and lateral bending of the spine.

The first inner surface 116 of the first end plate 110 can be parallel to the second inner surface 126 of the second end plate 120 when implant 100 is assembled and is in a neutral position (i.e., the position where the first end plate 110 has not rotated relative to the second end plate 120). Alternatively, the first inner surface 116 of the first end plate 110 can be non-parallel to the planar surface of the second inner surface 126 of the second end plate 120 when implant 100 is assembled and in a neutral position. This non-parallel orientation of the first end plate 110 and the second end plate 120 allows the plates to pivot to a greater degree with respect to each other. Additionally, other factors such as the height and position of the spacer 130, can also be adjusted in order to increase the degree that the first end plate 110 and the second end plate 120 can pivot relative to each other.

The embodiments shown in FIG. 1a and FIG. 1b illustrate the first and second keels 114,124, which include ports 148, 152, respectively, that facilitate bone ingrowth. For example, bone from the vertebral bodies can grow thorough the ports 148,152, and aid in securing the first and second keels 114, 124 and the implant 100 with respect to the vertebral bodies. In addition, surfaces defined by the first and second keels 114,124 and the first and second outer surfaces 112, 122 of implant 100 can be roughened in order to promote bone ingrowth into these defined surfaces of implant 100. In another embodiment the ports 148,152, the first and second keels 114,124, and the first and second outer surfaces 112, 122 of implant 100 can be coated with materials that promote bone growth such as for example bone morphogenic protein, BMP, or structural materials such as hyaluronic acid, HA, or other substance which promotes growth of bone relative to and into the keel, keel ports, and other external surfaces of the implant 100.

When implant 100 is inserted between vertebrae the planar surfaces corresponding to the first and second outer surfaces 112, 122 and the first and second inner surfaces 116, 126 of the first and second end plates 110, 120 lie within, or substantially within, the axial plane of the body of the patient. Similarly, the first and second keels 114, 124 are aligned in the axial plane, or perpendicular to the sagittal plane of the vertebrae.

FIG. 1B shows an alternative perspective view of implant 100 shown in FIG. 1A. Again, implant 100 has a first or upper end plate 110 that is configured to mate with a first vertebra and a second or lower end plate 120 that is configured to mate with a second vertebra. The first and second keels 114,124 extend into the vertebral bodies to anchor implant 100 into position, and are perpendicular to the median sagittal plane of the spine, in which extension and flexion occur. The first and second keels 114,124 in this orientation offer substantial stability during extension and flexion for implant 100 inserted between the vertebrae of a patient. Additionally, the first and second keels 114,124 in this embodiment are aligned with and support the axis of articulation of implant 100 defined by an RL to LL orientation. The axis of articulation of implant 100 defined by an RL to LL orientation will be discussed in more detail below. The spacer 130 separates the first end plate 110 from the second end plate 120. As evidenced from the perspective view of FIG. 1B, the perimeter shape of the upper and lower end plates 110,120 can be configured to correspond to the perimeter shape of a vertebral disk. As will be appreciated by those of ordinary skill in the art, the perimeter shape of the upper end plate 110 and the lower end plate 120 can be the same.

Figure 2A:
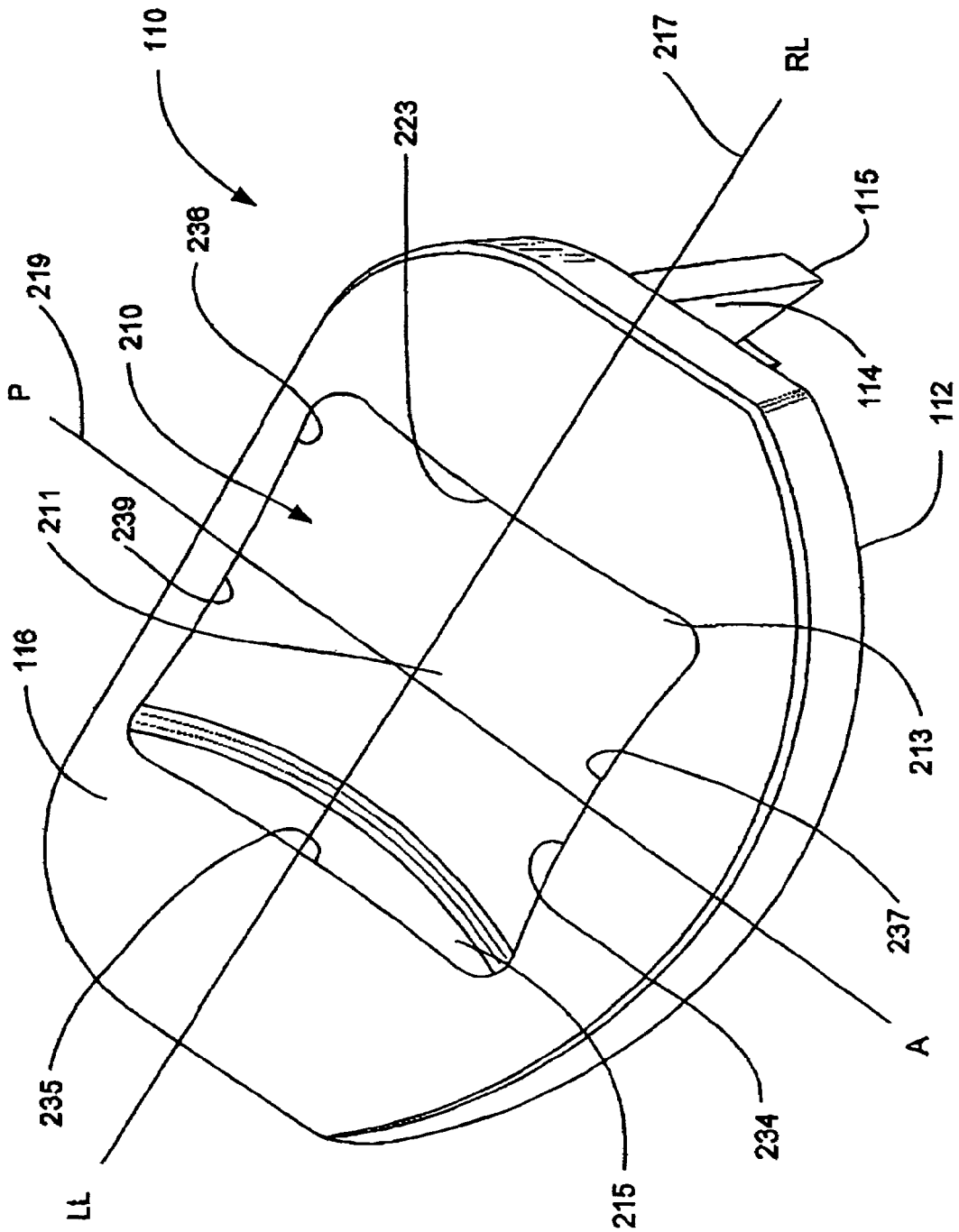
FIG. 2A and FIG. 2B show perspective views of the first and second inner surfaces of the first end plate and the second end plate of an embodiment of implant 100.

FIG. 2a shows a perspective view of an embodiment of the first inner surface 116 of the first or upper end plate 110 of implant 100. The first inner surface 116 of the upper end plate 110 has a first socket or first cavity 210 formed therein. In one embodiment, the first socket 210 has a concave hemi-cylindrical surface. In this embodiment, the first socket 210 includes the shallow concave surface 211 with first ends 213,215 that are substantially perpendicular to the first inner surface 116. Also indicated in FIG. 2a are two axes, 217,219. The first upper axis 217 intersects the first upper plate 110 in an RL to LL orientation. The second upper axis 219 is perpendicular to the first upper axis 217, and intersects the upper plate 110 in an A to P orientation. The first socket 210 allows the first end plate 110 to pivot or rotate on spacer 130, about a first upper axis 217 that is about perpendicular to the first ends 213,215. The ends 213,215 block motion of the spacer 130 about the second upper axis 219, perpendicular to the first upper axis 217. In this embodiment, it is noted that the first and second keels 114,124 are aligned with and support the first upper axis 217, which is an axis of articulation for first end plate 110 about the spacer 130 for this embodiment, and is an axis that is about perpendicular to the sagittal plane of the spine.

As can be seen in FIG. 2a, the first socket 210 in this embodiment includes first ends 213,215 that have crests 233, 235 respectively. The crests 233,235 project into the first socket 210. Additionally, concave surface 211 has edges 234, 236 with crests 237, 239, respectively. The crests 233, 235, 237, and 239 allow a loose fit between the spacer 130 and the first socket 210, which will be disused in more detail below.

Figure 2B:
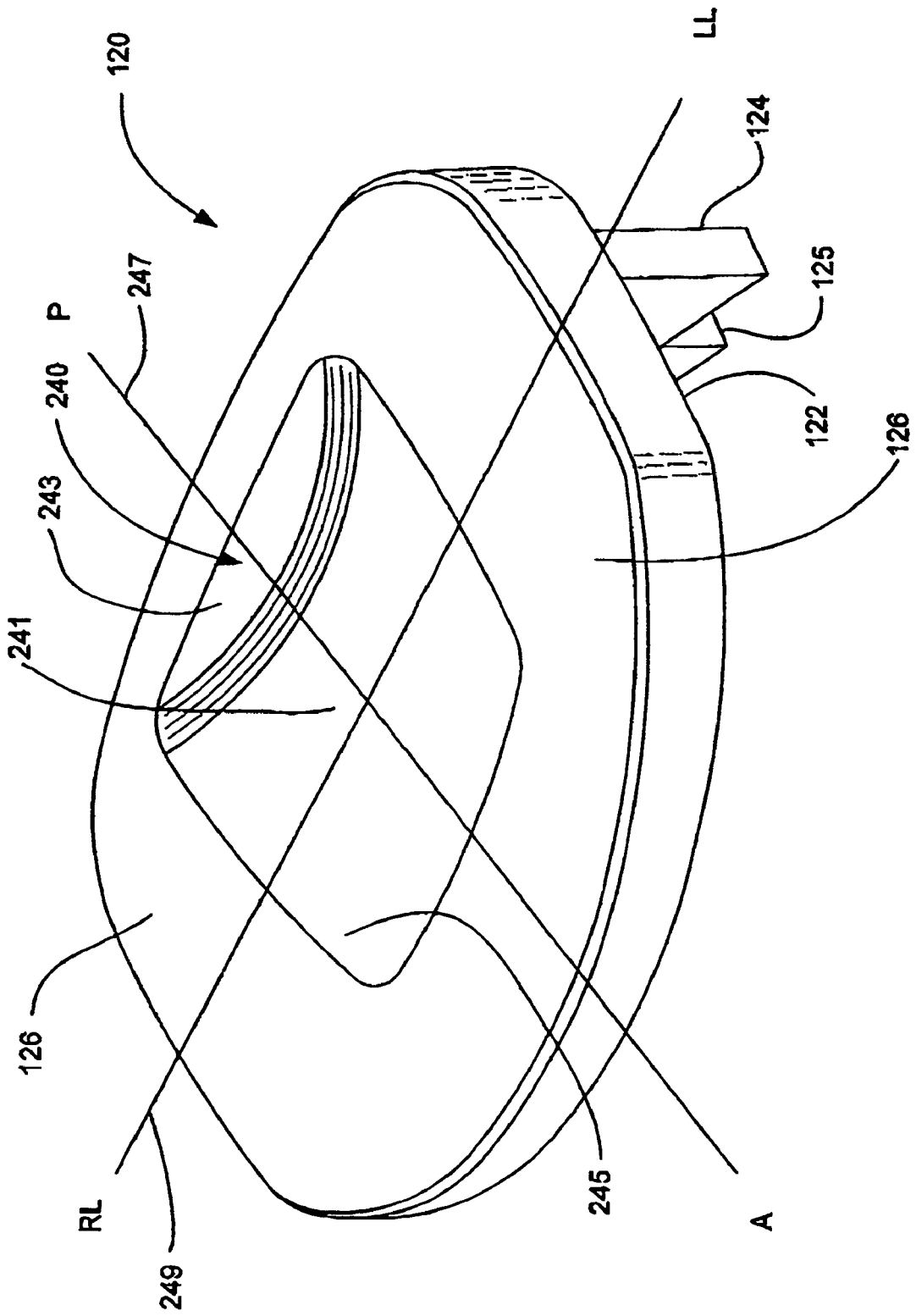

FIG. 2b shows a perspective view of an embodiment of the second or lower end plate 120 of implant 100. The second inner surface 126 of the lower end plate 120 has a second socket or second cavity 240 formed therein. In one embodiment, the second socket 240 has a concave hemi-cylindrical surface. In this embodiment, the second socket 240 includes the shallow concave surface 241 with second ends 243,245 that are substantially perpendicular to the second inner surface 126. Also indicated in FIG. 2b are two axes, 247,249. The first lower axis 247 intersects the first lower plate 120 in an A to P orientation. The second lower axis 249 is perpendicular to the first lower axis 247, and intersects the lower plate 120 in an RL to LL orientation. As will be described later with respect to the spacer 130, the second socket 240 allows the second end plate 120 to pivot or rotate on spacer 130, about the first lower axis 247 that is about perpendicular to the second ends 243,245. The ends 243,245 block motion of the spacer 130 about the second lower axis 249, perpendicular to the first lower axis 247. In this embodiment, it is noted that the second lower axis 249 is about parallel with first upper axis 217. As previously mentioned, the first and second keels 114,124 are aligned with and support the first upper axis 217, which is an axis of articulation of the upper end plate 110 about the spacer 130 for this embodiment, and is an axis that is about perpendicular to the sagittal plane of the spine, as is second lower axis 249. Further, the first lower axis 247 is an axis of articulation of the lower end plate 120 about the spacer 130, and the first lower axis 247 is perpendicular to the first upper axis 217.

The fit of the spacer in the first socket 210 and the second socket 240 can be loose so that the spacer allows the first end plate 110 to be able to twist somewhat relative to the second plate 120. This twisting action would generally be about an axis that is perpendicular to the first and second inner surfaces 116,126 of the first and second end plates 110,120, respectively. Thus, implant 100 of this embodiment allows the spine to have movement in three orthogonal degrees of freedom, namely (1) forward and backward bending movement, (2) lateral side-to-side bending, and (3) twisting movement. It is to be understood that the second socket 240 in the lower end plate 120 can also have the same design as the first socket 210 in the upper end plate 110 with an increase in the amount of twisting movement afforded by implant 100. As is noted previously herein, loose fit generally between one or both of first socket 210 and second socket 240 and the spacer 130 can allow for twisting motion. Further the spacer 130 can also be made with crests on the curved surfaces and on the ends in order to afford similar twisting motion. In other embodiments, the fit can be tighter in order to restrict such twisting action.

Figure 2C:
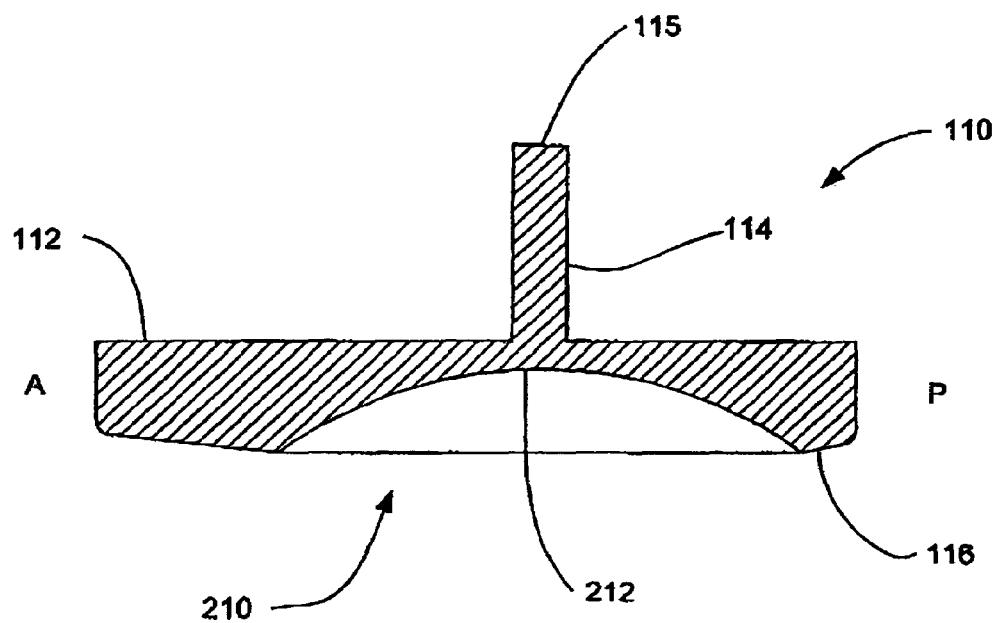
FIG. 2C through FIG. 2F show cross-sectional views of the first end plate and the second end plate of an embodiment of implant 100.
Figure 2D:
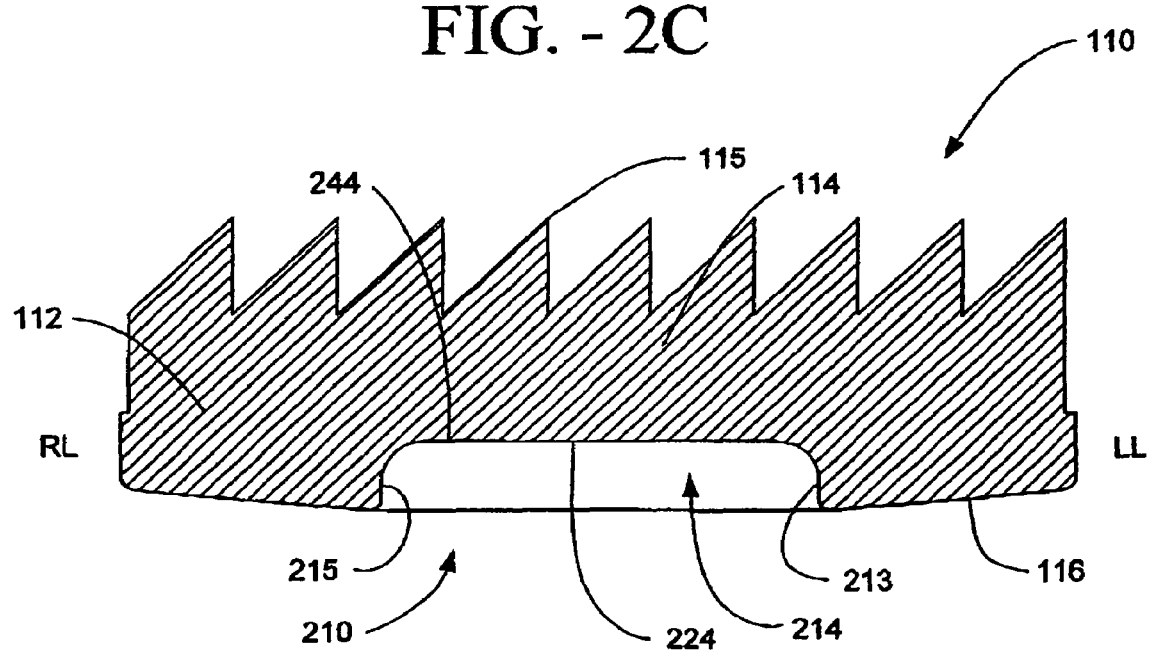
Figure 2E:
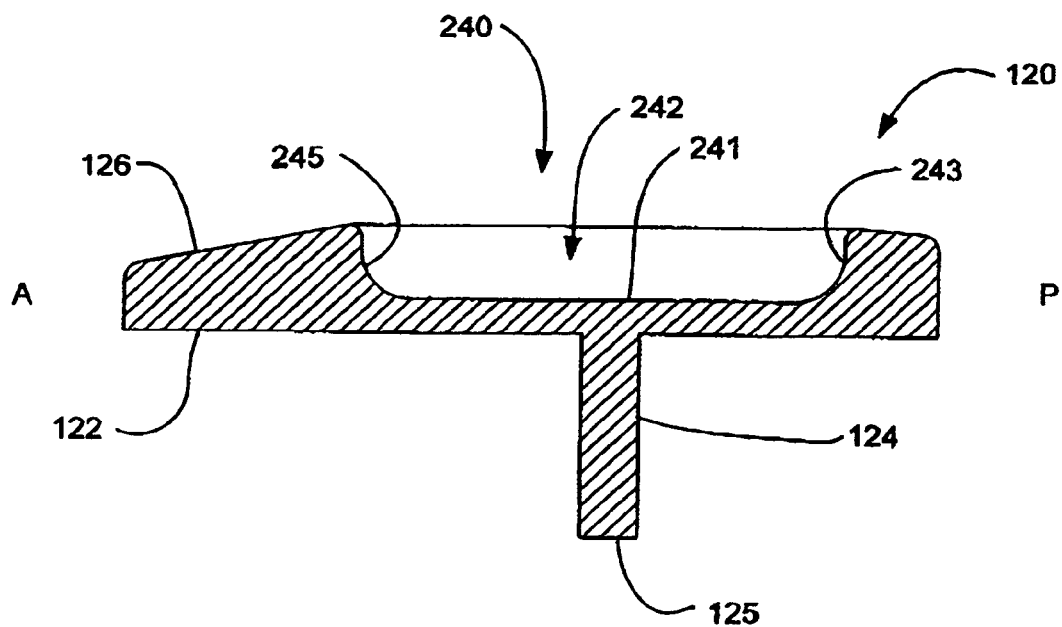
Figure 2F:
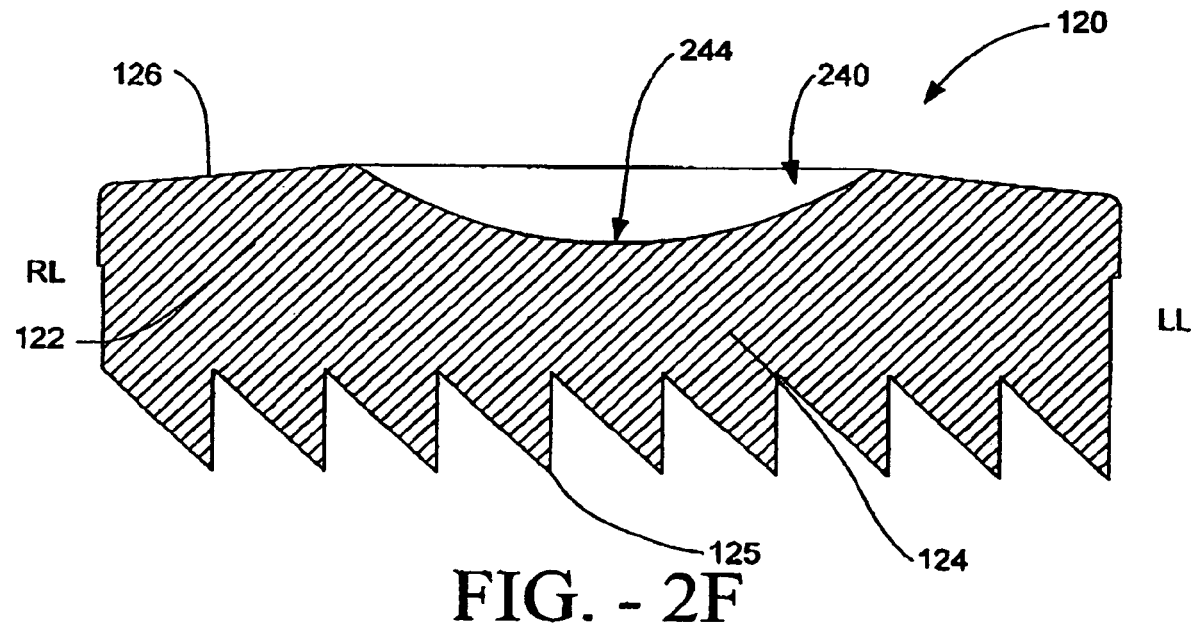

Turning now to FIG. 2c through FIG. 2f, the cross-sections of the upper and lower end plates 110,120 of an embodiment of implant 100 are shown. FIG. 2c illustrates the first dimension 212 of the first socket 210, and FIG. 2d illustrates the second dimension 214 of the first socket 210. The first dimension 212 and the second dimension 214 of the first socket 210 are perpendicular to each other. FIG. 2e illustrates that the first dimension 242 of the second socket 240, and FIG. 2f illustrates the second dimension 244 of the second socket 240. The first dimension 242 and the second dimension 244 of the second socket 240 are perpendicular to each other. FIGS. 2c and 2e are a cross-section taken along a plane that would correspond to a plane that is parallel to the median sagittal plane of the body after implant was inserted. FIG. 2d and FIG. 2f are a cross-section taken along a plane that would correspond to a plane that is parallel to the frontal (coronal) plane of the body after implant 100 was inserted.

For one embodiment, relative dimensions of the first and second sockets 210,240 are indicated in FIG. 2c through FIG. 2f. As previously discussed, the first and second outer surfaces 112,122 of the first and second end plates 110,120 are configured to contact vertebral bodies when implant 100 is inserted between vertebrae. The first and second outer surfaces 112,122 have first and second keels 114,124 that extend into the vertebral body when implant 100 is inserted between vertebrae. The first and second inner surfaces 116,126 of the upper and lower end plates 110,120 have first and second sockets 210,240 formed therein.

In FIG. 2c, the first socket 210 has a first dimension 212. In the first dimension 212, the first socket 210 is concave such that it is curved like the inner surface of a cylinder. In FIG. 2d, the second dimension 214 is in the form of a trough or "flattened-U" with a previously indicated concave bottom surface 211 and two ends or sidewalls 213, 215. As shown in FIG. 2d, the ends or sidewalls 213, 215 are parallel to each other and perpendicular to the bottom surface 211. However, as will be appreciated by those of ordinary skill in the art, the ends or sidewalls 213, 215 can be formed at an angle relative to each other without departing from the scope of what is disclosed.

In FIG. 2e, the second socket 240 has a first dimension 242. The first dimension 242 is in the form of a trough or "flattened-U" with a bottom concave surface 241 and two ends or sidewalls 243,245. As shown in FIG. 2f, the ends or sidewalls 243, 245 are parallel to each other and perpendicular to the bottom surface 241. However, as will be appreciated by those of ordinary skill in the art, the ends or sidewalls 243, 245 can be formed at an angle relative to each other without departing from the scope of what is disclosed. In FIG. 2f, the second dimension 242 of the second socket 240 is concave such that it is curved like the inner surface of a cylinder.

As previously mentioned, FIG. 2c and FIG. 2d are oriented to illustrate that the first dimension 212 shown in FIG. 2c and the second dimension 214 shown in FIG. 2d are perpendicular to each other, while FIG. 2e and FIG. 2f illustrate that the first dimension 242 is perpendicular to second dimension 244. Further, the curved first dimension 212 of FIG. 2c is oriented perpendicularly to the curved second dimension 244 of FIG. 2f, while the trough dimension 214 of FIG. 2d is oriented perpendicularly to the trough dimension 242 of FIG. 2e. It is noted that in FIGS. 2c through 2f that the first inner and second inner surfaces 116,126 of the first and second plates 110,120 are not parallel as shown in FIG. 1a and FIG. 1b, for example. In FIGS. 2c through 2f the surfaces slope away from the first and second sockets 210,240, respectively, in order to provide for a larger range of motion between the first and second plates.

Figure 3A:
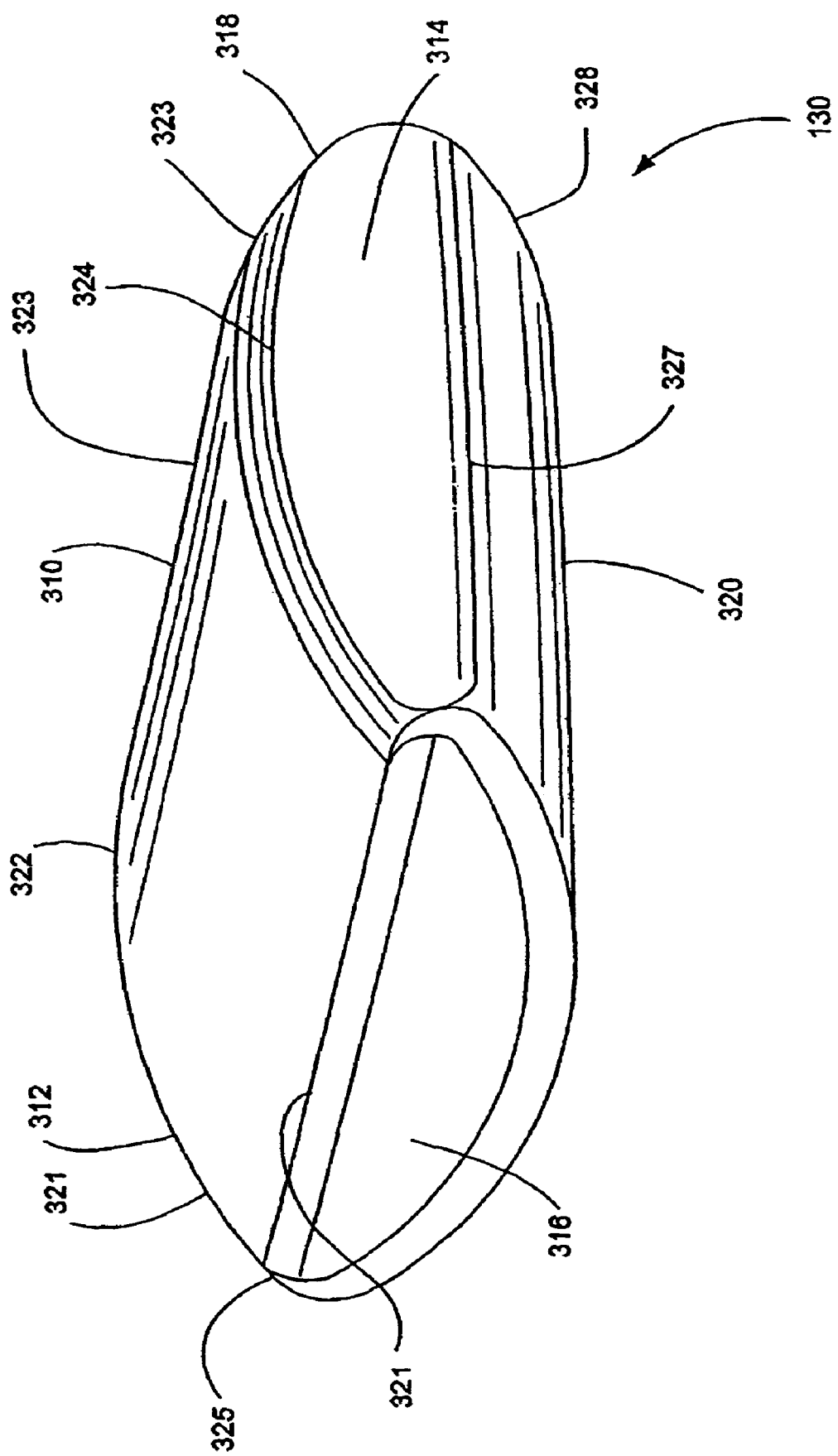
FIG. 3A is a perspective view of a spacer of an embodiment of implant 100.

In FIG. 3a, the spacer 130 is depicted in perspective view. The spacer 130 is dimensioned so that it has a curved or convex upper surface 310 and a curved or convex lower surface 320, respectively, corresponding with the opposing concave surfaces in the upper end plate 110 and the lower end plate.

As shown in FIG. 3a, the curved upper surface 310 is bordered along its curved edge by a pair of first sides 312, 314 that are parallel to each other and along its flat edge by a pair of second sides 316, 318 that are parallel to each other and perpendicular to the pair of first sides 312, 314. The orientation of the pair of first sides 312, 314 to the pair of second sides 316, 318 is such that the curved upper edges 322, 324 of the first sides 312, 314 extend toward the ends of the flat edges 321, 323 of the pair of second sides 316, 318. The curved lower edges 326, 328 extend to meet the ends of the flat edges 325, 327 of the first sides 312, 314.

Figure 3B:
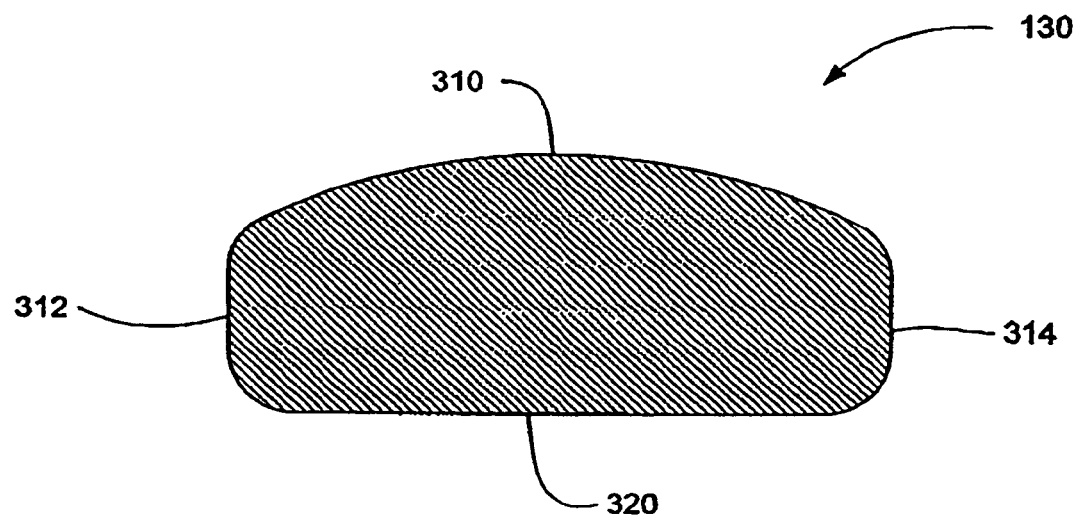
FIG. 3B and FIG. 3C are cross-sections of the spacer of an embodiment of implant taken at 90° angles respective to each other.
Figure 3C:
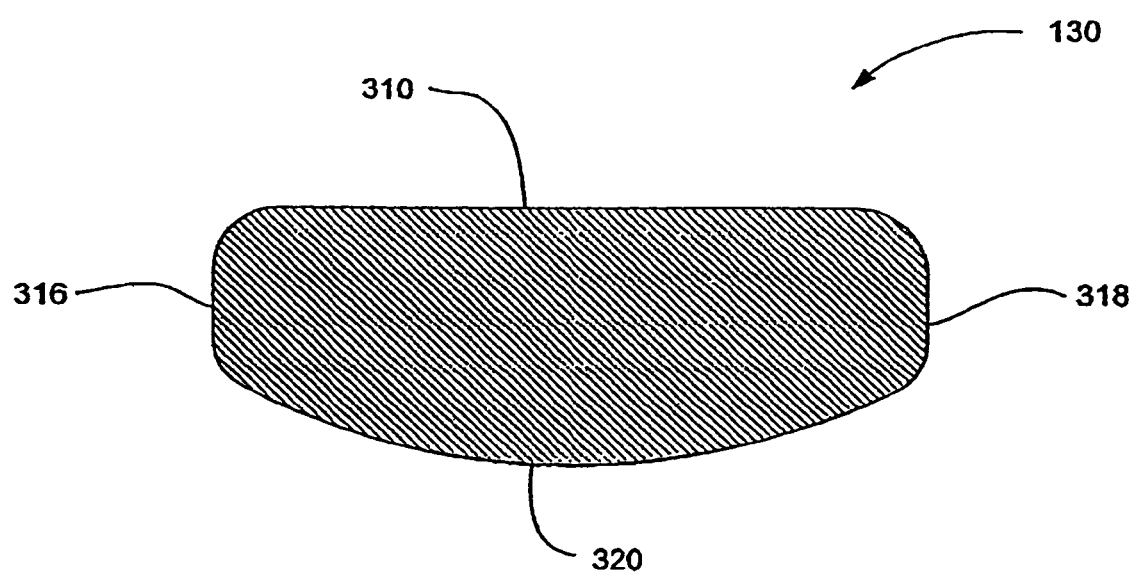

FIG. 3b and FIG. 3c show cross-sections of the spacer 130, shown in FIG. 3a. The cross-section of FIG. 3b is taken at a 90° angle from the cross-section shown in FIG. 3c. FIG. 3b is taken through a plane parallel to the ends 312, 314 and FIG. 3c is taken through a plane parallel to ends 316, 318. The spacer 130 has a concave upper surface 310 and a concave lower surface 320 and pairs of parallel sides 312, 314 and 314, 318.

Figure 4A:
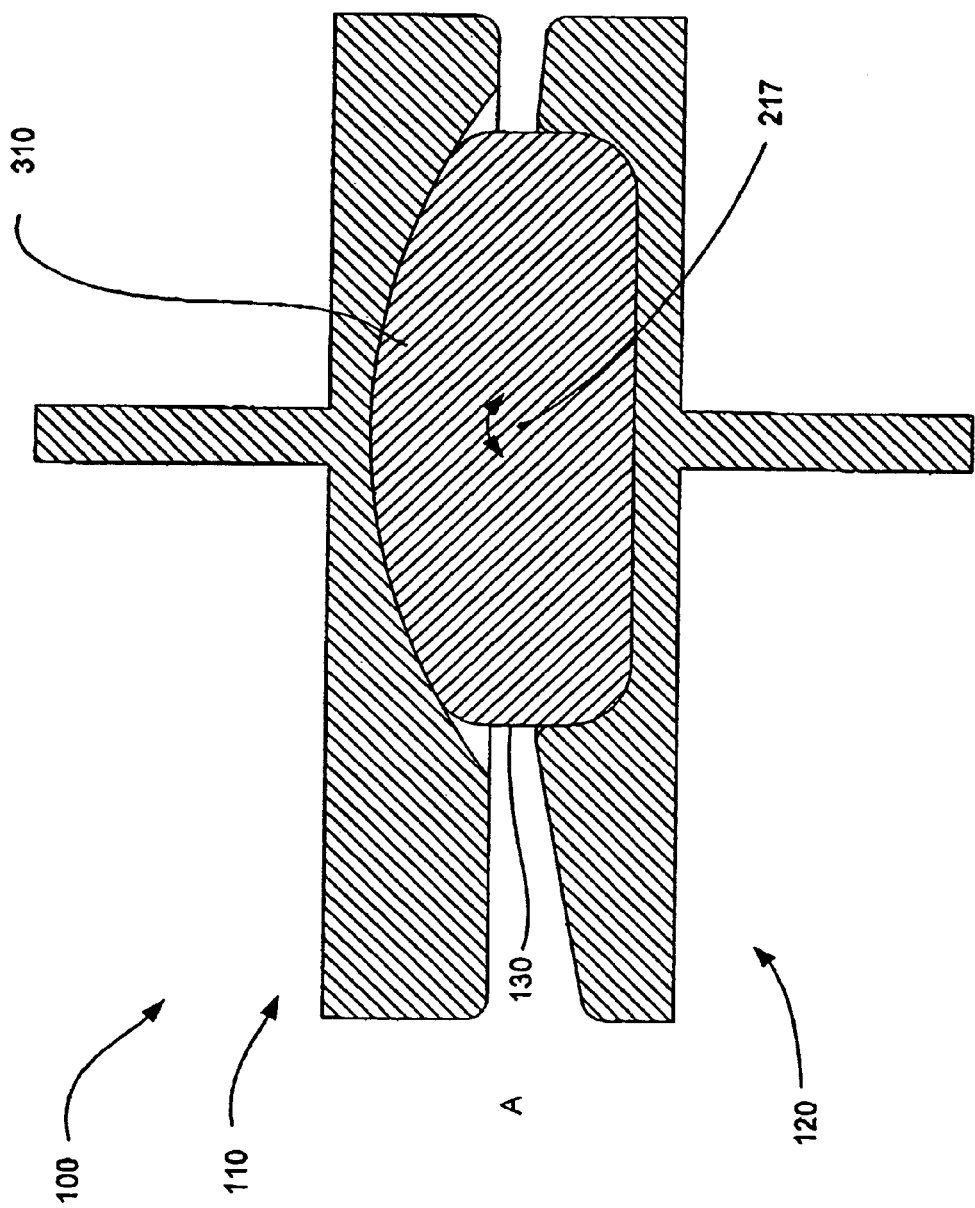
FIG. 4A is a cross-section of an embodiment of implant 100 taken along a plane parallel to the sagittal plane.
Figure 4B:
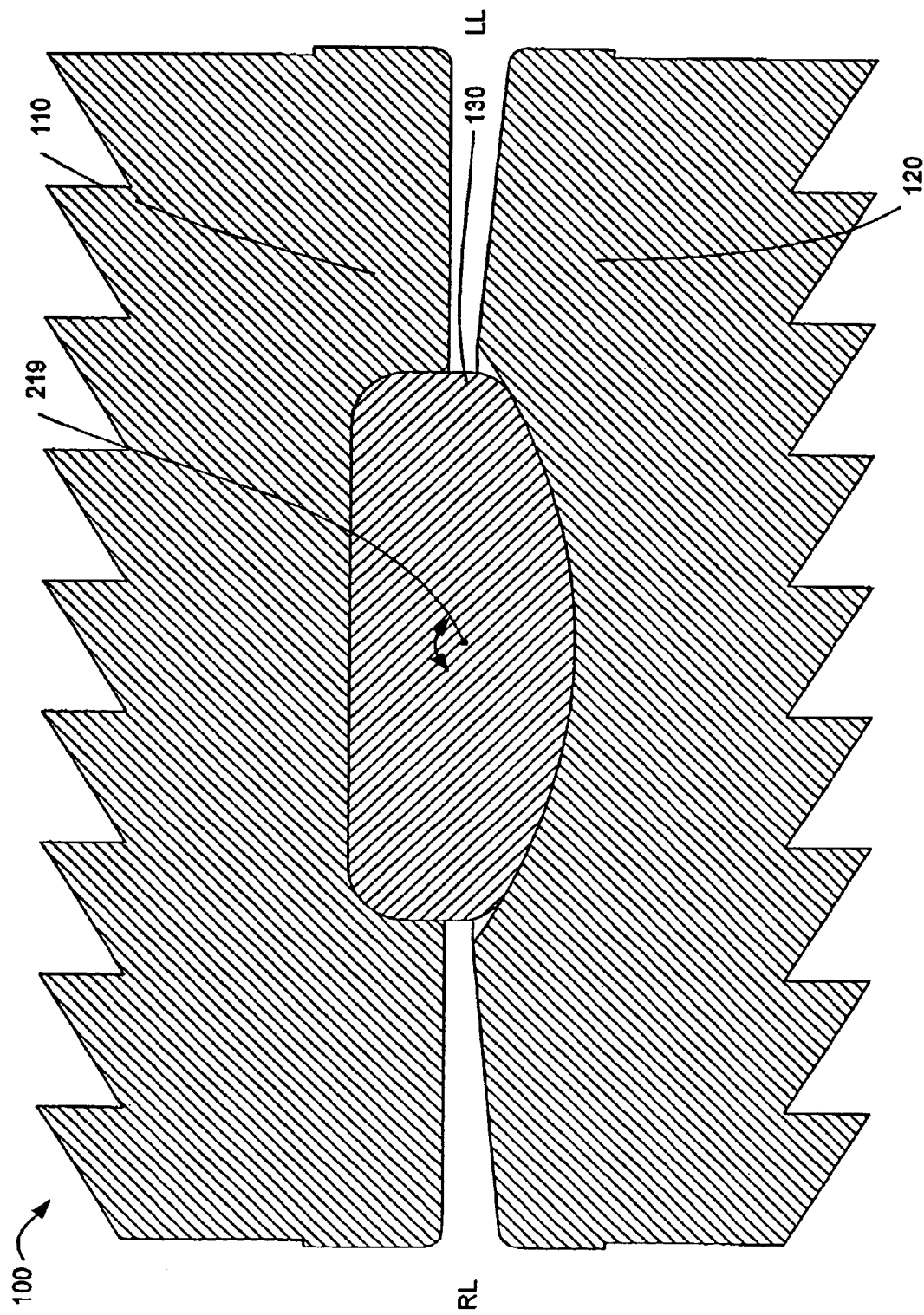
FIG. 4B is a cross-section of an embodiment of implant corresponding to a plane parallel to the location of the coronal plane, or perpendicular to the sagittal plane of the vertebrae after implant 100 has been inserted.

FIG. 4a and FIG. 4b show sections for an embodiment of implant 100. FIG. 4a shows a cross-section of implant 100 in its assembled condition taken along a plane that would correspond to a plane that is parallel to the median sagittal plane of the body of a patient after implant 100 was inserted. FIG. 4b shows a cross-section of implant 100 in its assembled condition taken at 90° from the cross-section shown in FIG. 4a, which is parallel to the frontal (coronal) plane, or perpendicular to the sagittal plane of the body of a patient after implant 100 was inserted. The implant 100 has a first upper end plate 110 that is configured to mate with a first vertebra and a second lower end plate 120 that is configured to mate with a second vertebra. The spacer 130 sits between the upper end plate 110 and the lower end plate 120. As previously mentioned, the first upper axis 217 is an axis of articulation for first end plate 110 about the spacer 130 for this embodiment, while the first lower axis 247 is an axis of articulation of the lower end plate 120 about the spacer 130. Further, first upper axis 217 is perpendicular to the first lower axis 247. FIG. 4a, in particular, indicates how the first and second keels, 114,124, are aligned with and support the lateral axis of articulation defined by the first upper axis 217. The first and second keels 114,124 in this orientation offers substantial stability during extension and flexion for implant 100 inserted between the vertebrae of a patient. As in all of the embodiments described herein, the keels are about perpendicular to the sagittal plane of the body of a patient and suitable for lateral insertion into the spine of a patient.

Figure 5A:
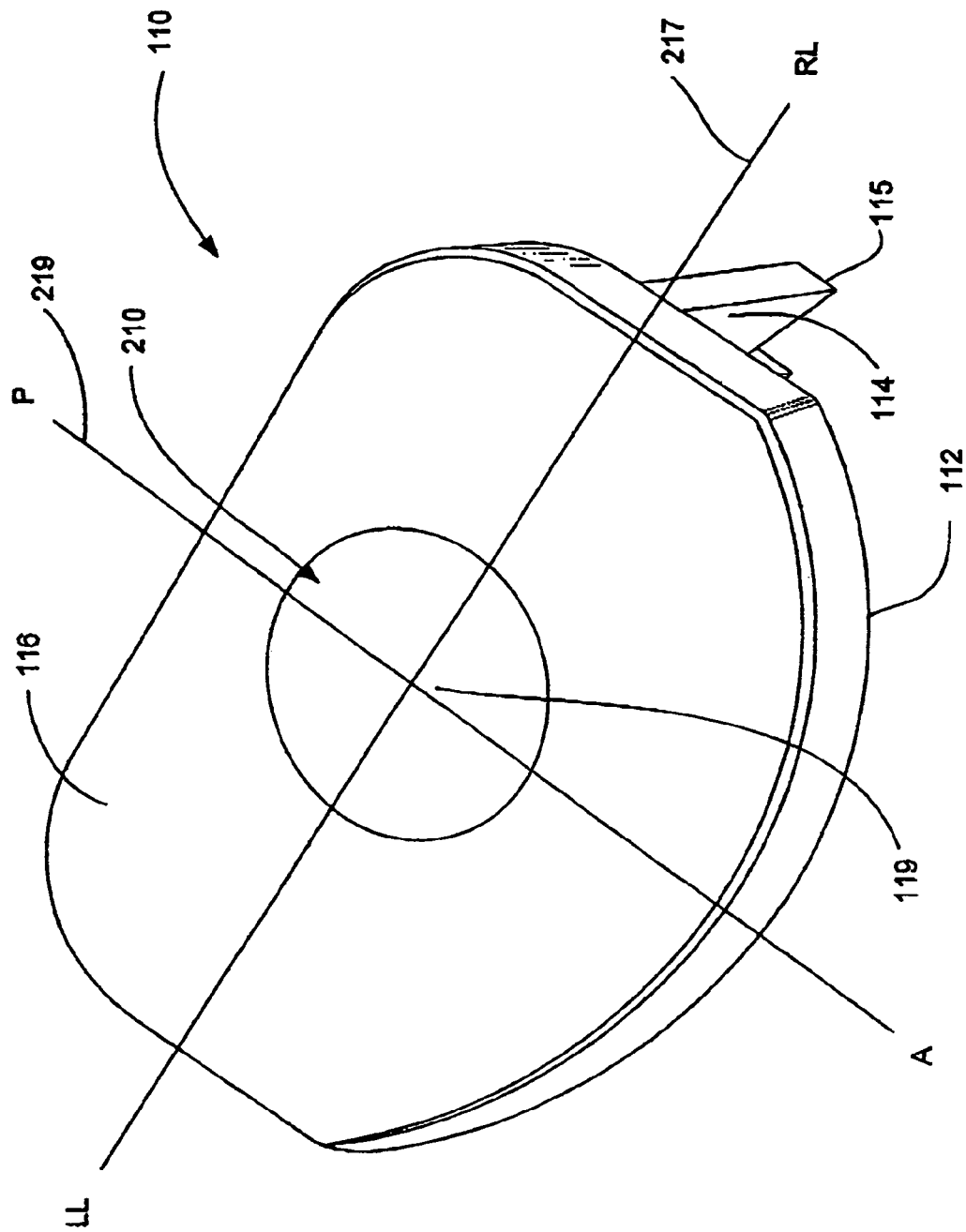
FIG. 5A and FIG. 5B show perspective views of the first and second inner surfaces of the first end plate and the second end plate of another embodiment of implant 100.
Figure 5B:
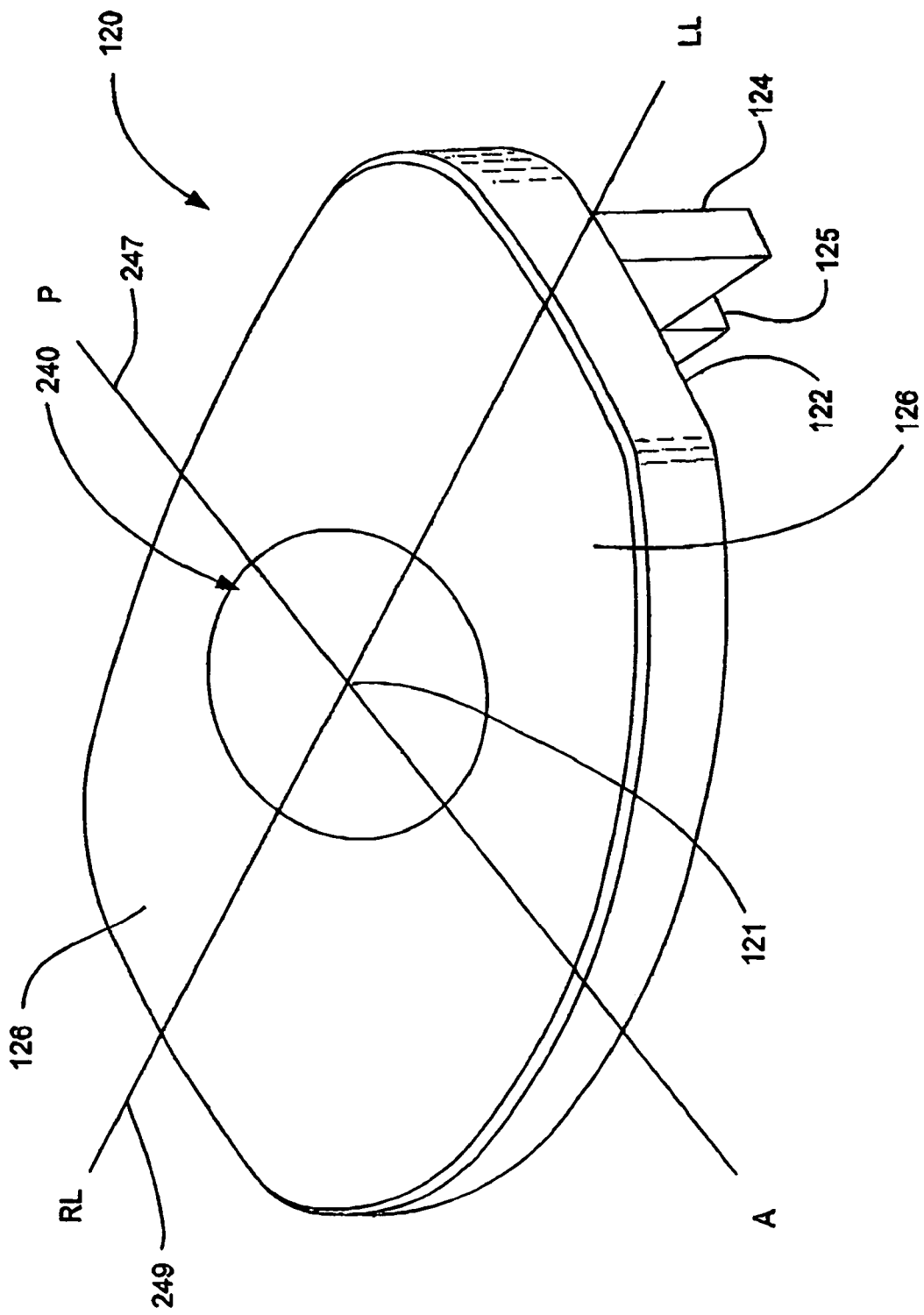
Figure 5C:
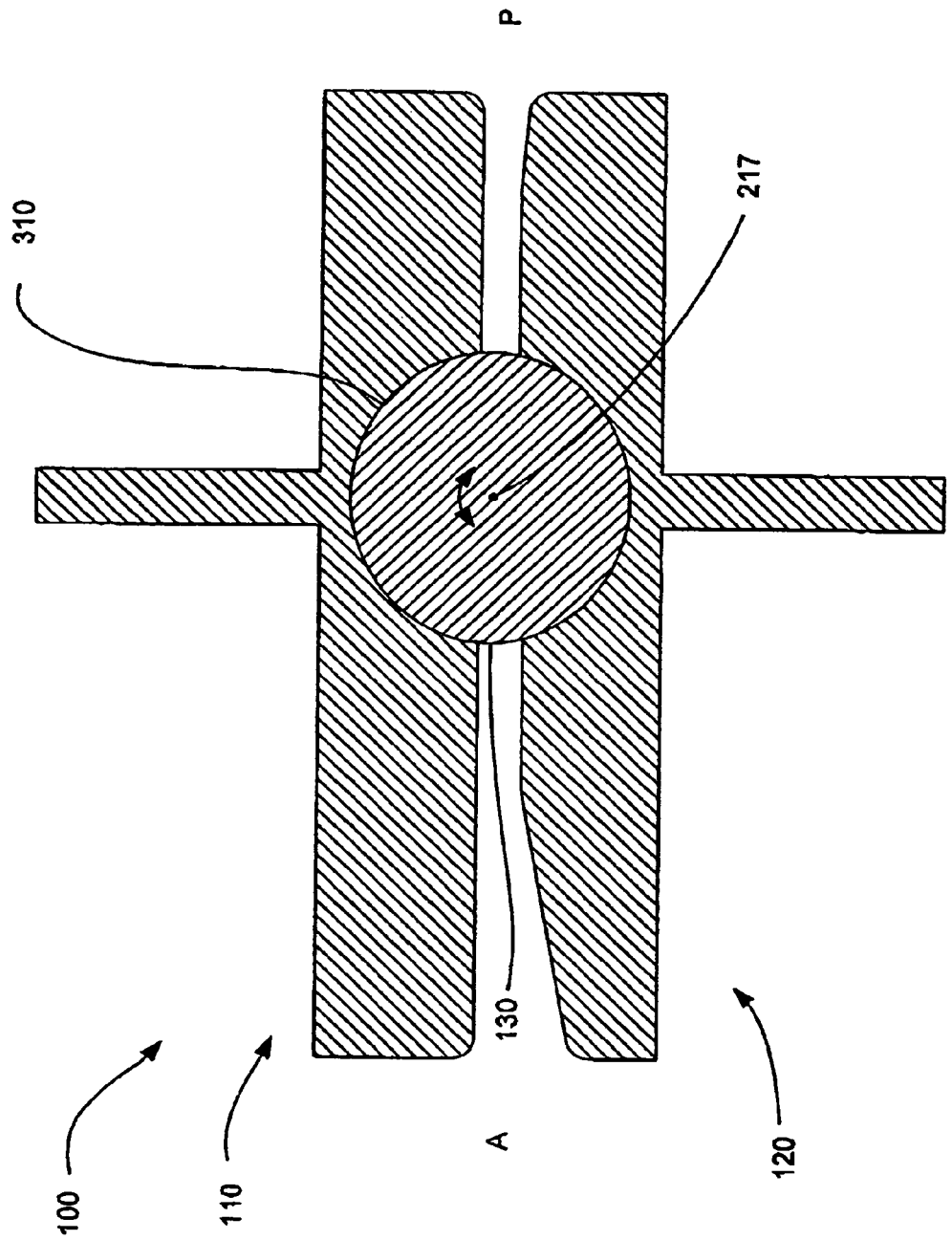
FIG. 5C is a cross-section of the embodiment of implant 100 taken along a plane parallel to the sagittal plane.
Figure 5D:
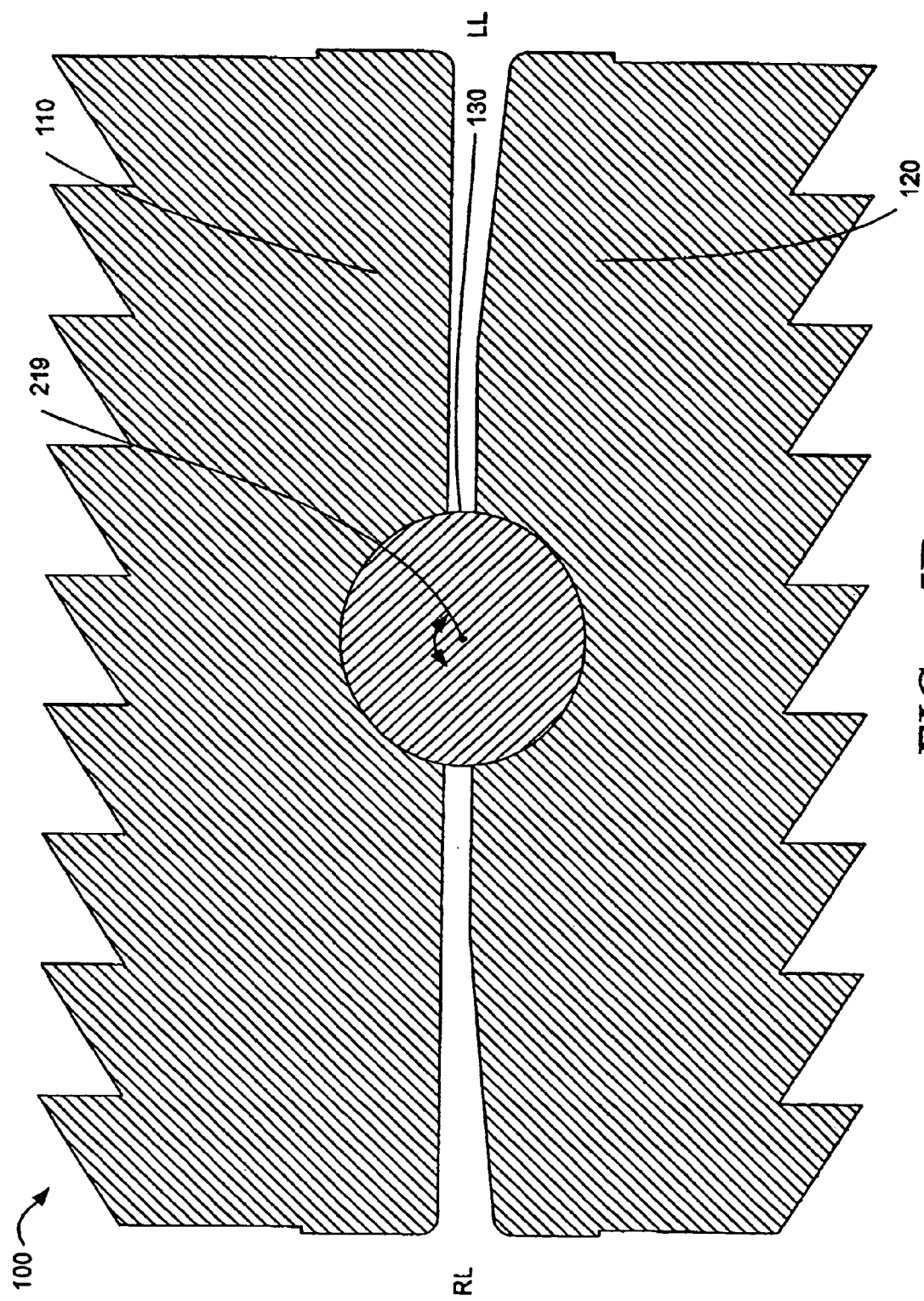
FIG. 5D is a cross-section of the embodiment of implant 100 corresponding to a plane parallel to the location of the coronal plane, or perpendicular to the sagittal plane of the vertebrae after implant 100 has been inserted.

FIG. 5a through FIG. 5c show representations for an another embodiment of implant 100. FIG. 5a and FIG. 5b show the first and second inner surfaces, 116,126, of the first and second endplates of another embodiment of implant 100. It should be noted that this additional embodiment of Implant 100 has the features described previously described for FIG. 2a and FIG. 2b. Similarly, FIG. 5c and FIG. 5d are sections that are analogous to the sections of a first embodiment shown for FIG. 4a and FIG. 4b, respectively.

FIG. 5a shows a perspective view of an embodiment of the first inner surface 116 of the first or upper end plate 110 of implant 100. The first inner surface 116 of the upper end plate 110 has a first socket or first cavity 210 formed therein. In the embodiment of FIG. 5a, the first socket 210 has a concave hemispherical surface. Indicated in FIG. 5a are two axes, 217,219. The first upper axis 217 intersects the first upper plate 110 in an RL to LL orientation. The second upper axis 219 is perpendicular to the first upper axis 217, and intersects the upper plate 110 in an A to P orientation. The two axes intersect at first, or upper point 119. The first socket 210 allows the first end plate 110 to pivot or rotate on spacer 130 about the first point 119. FIG. 5b shows a perspective view of an embodiment of the second inner surface 126 of the second or lower end plate 120 of implant 100. The second inner surface 126 of the lower end plate 120 has a second socket or first cavity 240 formed therein. In the embodiment of FIG. 5b, the second socket 240 has a concave hemispherical surface. Indicated in FIG. 5b are two axes, 247,249. The first lower axis 247 intersects the second, or lower plate 120 in an RL to LL orientation. The second lower axis 249 is perpendicular to the first upper axis 247, and intersects the lower plate 120 in an A to P orientation. The two axes intersect at second, or lower point 121. The second socket 240 allows the second lower end plate 120 to pivot or rotate on spacer 130, about the lower point 121.

In the alternative embodiment shown in FIG. 5a and FIG. 5b, it is noted that the first and second keels 114,124 are aligned with and support the first and second points and 119, 121, which are an points of articulation for first end plate 110 and the second end plate, respectively about the spacer 130 for this embodiment. The keels are oriented so as to be about perpendicular to the sagittal plane of a patient when the implant is inserted using a lateral approach.

FIG. 5c shows a cross-section of implant 100 in its assembled condition taken along a plane that would correspond to a plane that is parallel to the median sagittal plane of the body of a patient after implant 100 was inserted. FIG. 5d shows a cross-section of implant 100 in its assembled condition taken at 90° from the cross-section shown in FIG. 5c, which is parallel to the frontal (coronal) plane, or perpendicular to the sagittal plane of the body of a patient after implant 100 was inserted. The implant 100 has a first upper end plate 110 that is configured to mate with a first vertebra and a second lower end plate 120 that is configured to mate with a second vertebra. The spacer 130 sits between the upper end plate 110 and the lower end plate 120. As previously mentioned, the first and second upper axes 217,219 define a first point of articulation for first end plate 110 about the spacer 130 for this embodiment, while the first and second lower axes 247,249 define a second point of articulation of the lower end plate 120 about the spacer 130. FIG. 5c and FIG. 5d indicate how the first and second keels, 114,124, are aligned with and support the first and second points of articulation 119,121. The first and second keels 114,124 in this orientation offer substantial stability during extension and flexion for implant 100 inserted between the vertebrae of a patient.

It is to be understood that the embodiments of the disclosed implant can be made of medical grade titanium, stainless steel or cobalt chrome. Other materials that have appropriate structural strength and that are suitable for implantation into a patient can also be used.

Alternatively, the spacer 130 can be made out of a polymer, and more specifically, the polymer is a thermoplastic with the other components made of the materials specified above. Still more specifically, the polymer is a polyketone known as polyetheretherketone (PEEK). Still more specifically, the material is PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com). The spacer 130 can be formed by extrusion, injection, compression molding and/or machining techniques. This material has appropriate physical and mechanical properties and is suitable for carrying and spreading the physical load between the spinous process. Further in this embodiment, the PEEK has the following additional approximate properties:

| Property | Value |
| --- | --- |
| Density | 1.3 g/cc |
| Rockwell M | 99 |
| Rockwell R | 126 |
| Tensile Strength | 97 Mpa |
| Modulus of Elasticity | 3.5 Gpa |
| Flexural Modulus | 4.1 Gpa |

It should be noted that the material selected may also be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

The spacer can also be comprised of polyetherketoneketone (PEKK). Other material that can be used include polyetherketone (PEK), polyetherketoneether-ketoneketone (PEKEKK), and polyetheretherketoneketone (PEEKK), and, generally, a polyaryletheretherketone. Further, other polyketones can be used as well as other thermoplastics.

Reference to appropriate polymers that can be used in the spacer can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials."

In operation, implant 100 enables a forward bending movement and a rearward bending movement by sliding the upper end plate 110 forward and backward over the spacer 130 relative to the lower end plate 120. This movement is shown as rotation about the axis 217 in FIG. 4a and FIG. 4c.

The implant 100 enables a right lateral bending movement and a left lateral bending movement by sliding the lower end plate 120 side-to-side over the spacer 130 relative to upper end plate 110. This movement is shown as rotation about the axis 219 in FIG. 4b and FIG. 4d. Additionally, with a loose fit between the first end plate, the second end plate and the spacer, rotational or twisting motion along an axis that is along the spine and perpendicular to the first and second plates is accomplished.

Figure 6:
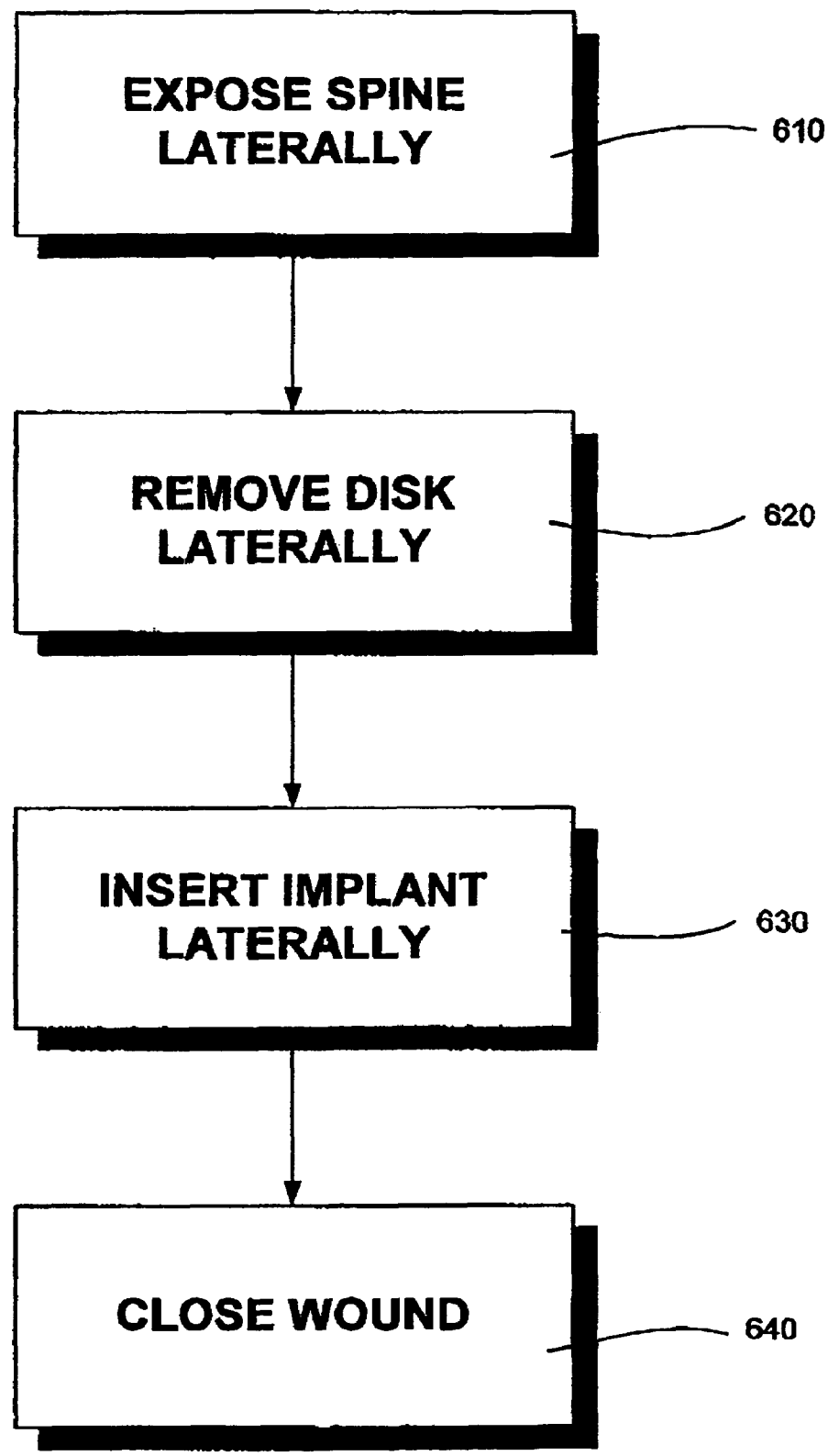
FIG. 6 is a block diagram showing the method steps for the lateral implantation of an embodiment of the disclosed the disclosed implant.

FIG. 6 is a block diagram showing the basic steps of the method of laterally inserting the implant 100. First the spine is exposed through a lateral access 610, then the intervertebral disk is removed if necessary laterally 620. The implant is then inserted laterally 630 between two vertebrae and the wound is closed 640. This procedure can be followed for either a left lateral approach or right lateral approach. For a left lateral approach, the teeth 115,125 of upper and lower keels 114, 124 would be pointed towards the left lateral face of the device in order to aid in retaining implant 100 in place. For a right lateral approach, the teeth would point towards the right lateral face of the device.

Additional steps, such as cutting channels into the vertebral bodies to accept the first and second keels 114,124 of the first and second end plates 110,120 and assembling implant 100 by inserting the spacer 130 between the upper and lower end plates 110,120 prior to installation can also be performed without departing from the scope of what is disclosed.

It is to be appreciated that although the first and second plates are depicted as having concave cavities and the spacer is depicted as having two convex surfaces that are oriented about perpendicular to each other, that other embodiments the disclosed implant can have other configurations. For example, the first and second plates can have convex protrusions, such as, for example, cylindrical protrusions that are shaped to mate with concave surfaces of a spacer, with the concave surfaces of the spacer oriented about perpendicular to each other. In this embodiment, the convex protrusions of the first and the second plates could preferably each have a pair of parallel side walls that would act as the side walls in the depicted embodiments in order to block motion of the spacer. Also, it is to be appreciated that in still another embodiment, the spacer can have upper and lower truncated convex spherical surfaces with two pairs of side walls, instead of cylindrical surfaces with side walls, and be in the scope and spirit of what is disclosed herein. In this embodiment, each of the first and second plates would have truncated concave spherical surfaces with a pair of side walls. In still a further embodiment, each of the first and second plates could have spherical protrusions with a pair of side walls and the spacer could have first and second spherical concave surfaces with two pairs of side walls joining the first and second spherical concave surfaces. Still alternatively, the first end plate can have a concave surface and blocking side walls and the mating portion of the spacer can be convex with the second plate having a convex protrusion with the mating portion of the spacer, or being concave, with blocking side walls.

What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the embodiments described herein, thereby enabling others skilled in the art to understand the various embodiments and various modifications that are suited to the particular use contemplated. It is intended that the scope of what is disclosed be defined by the following claims and their equivalence.

What is claimed:

1. An intervertebral implant comprising:
    an articulating unit further comprising;
        a first end plate with a first inner concave cylindrical surface;
        a second end plate with a second inner concave cylindrical surface opposing the first inner concave cylindrical surface; and
        an articulating element positioned between the first end plate and the second end plate, wherein the articulating element has four side walls and an upper convex cylindrical surface and a lower convex cylindrical surface oriented perpendicular to the upper convex cylindrical surface, wherein the upper convex cylindrical surface has an outer perimeter interfacing with all four side walls, wherein the lower convex cylindrical surface has an outer perimeter interfacing with all four side walls, wherein the upper convex cylindrical surface is adapted to fit at least partially in the first inner cylindrical surface and the lower convex cylindrical surface is adapted to fit at least partially in the second inner cylindrical surface; and
    an attachment mechanism adapted to engage an adjacent vertebral body, wherein the attachment mechanism extends from the articulating unit along a lateral direction with respect to the vertebral body.

2. The intervertebral implant of claim 1 wherein the articulating element allows the first end plate to pivot about the upper convex cylindrical surface in association with bending between flexion and extension, and the second end plate to pivot about the lower convex cylindrical surface in association with lateral bending.

3. The intervertebral implant of claim 1 wherein the attachment mechanism is aligned with and supports the articulating element.

4. The intervertebral implant of claim 1 further comprising:
    the first inner surface with a first concave socket formed therein;
    the second inner surface with a second concave socket formed therein; and
    the upper and lower surfaces of the articulating element at least partially received in the first concave socket and the second concave socket.

5. An intervertebral implant comprising:
    a first end plate adapted to mate with a first vertebrae further comprising:
        a first inner concave cylindrical surface;
        a first outer surface; and
        at least one keel on the first outer surface, where the keel is perpendicular to the sagittal plane of the vertebral body;
    a second end plate adapted to mate a second vertebral body further comprising;
        a second inner concave cylindrical surface, wherein the first inner surface and the second inner surface oppose one another;
        a second outer surface; and
    a spacer positioned between the first end plate and the second end plate, wherein the spacer has four side walls and an upper convex cylindrical surface and a lower convex cylindrical surface oriented perpendicular to the upper convex cylindrical surface, wherein the upper convex cylindrical surface has an outer perimeter interfacing with all four side walls and the lower convex cylindrical surface has an outer perimeter interfacing with all four side walls, wherein the upper convex surface is adapted to fit at least partially in the first inner concave cylindrical surface and the lower convex cylindrical surface is adapted to fit at least partially in the second inner surface.

6. The intervertebral implant of claim 5 wherein the spacer allows the first end plate to pivot about the upper convex cylindrical surface in association with bending between flexion and extension, and the second end plate to pivot about the lower convex cylindrical surface in association with lateral bending.

7. The intervertebral implant of claim 5 wherein the keel is aligned with and supports the spacer.

8. The intervertebral implant of claim 5 further comprising at least one keel on the second outer surface.

9. The intervertebral implant of claim 8 wherein the keel is aligned with and supports the spacer.

10. The intervertebral implant of claim 5 further comprising:
the first inner surface with a first socket formed therein;
the second inner surface with a second socket formed therein; and
the spacer at least partially received in the first socket and the second socket.

11. An intervertebral implant comprising:
a first end plate adapted to mate with a first vertebrae further comprising:
a first inner concave cylindrical surface;
a first outer surface; and
at least one keel on the first outer surface, where the keel is perpendicular to the sagittal plane of the vertebral body;
a second end plate adapted to mate a second vertebrae further comprising;
a second inner concave cylindrical surface opposing the first inner surface;
a second outer surface; and
at least one keel on the second outer surface, where the keel is perpendicular to the sagittal plane of the vertebral body, and
a spacer positioned between the first end plate and the second end plate, wherein the spacer has four side walls and an upper convex cylindrical surface and a lower convex cylindrical surface oriented perpendicular to the upper convex cylindrical surface, wherein the upper convex cylindrical surface has an outer perimeter interfacing with all four side walls and the lower convex cylindrical surface has an outer perimeter interfacing with all four side walls, wherein the upper convex surface is adapted to fit at least partially in the first inner cylindrical concave surface and the lower convex surface is adapted to fit at least partially in the second inner cylindrical surface.

12. The intervertebral implant of claim 11 wherein the spacer allows the first end plate to pivot about the upper convex cylindrical surface in association with bending between flexion and extension, and the second end plate to pivot about the lower convex cylindrical surface in association with lateral bending.

13. The intervertebral implant of claim 11 wherein the keels on the first outer surface and the second outer surface are aligned with and support the spacer.

14. The intervertebral implant of claim 11 further comprising:
the first inner surface with a first socket formed therein;
the second inner surface with a second socket formed therein; and
the spacer at least partially received in the first socket and the second socket.

15. An interspinous disk replacement implant having an articulation unit with a first end plate having a first inner surface with a first concave cylindrical socket therein, a second end plate having a second inner surface opposing the first inner surface, the second inner surface with a second concave cylindrical socket therein, and an articulation element at least partially received in the first and second concave cylindrical socket, wherein the articulating element has four side walls and an upper convex cylindrical surface and a lower convex cylindrical surface oriented perpendicular to the upper convex cylindrical surface, wherein the upper convex cylindrical surface has an outer perimeter interfacing with all four side walls and the lower convex cylindrical surface has an outer perimeter interfacing with all four side walls, wherein the upper convex cylindrical surface is adapted to fit at least partially in the first inner surface and the lower convex cylindrical surface is adapted to fit at least partially in the second inner surface, the improvement of the implant comprising the implant having at least one keel extending from the articulation unit that is substantially perpendicular to the sagittal plane of the spine.

16. An interspinous disk replacement implant having a first end plate, a second end plate, and an articulation element between the first end plate and the second end plate, wherein the articulating element has four side walls and an upper convex cylindrical surface and a lower convex cylindrical surface oriented perpendicular to the upper convex cylindrical surface, wherein the upper convex cylindrical surface has an outer perimeter interfacing with all four side walls and the lower convex cylindrical surface has an outer perimeter interfacing with all four side walls, wherein the upper convex cylindrical surface is adapted to fit at least partially in the first end plate and the lower convex cylindrical surface is adapted to fit at least partially in the second end plate, the improvement comprising the implant having an attachment mechanism extending from the articulating unit that is aligned with and supports the articulation element, the attachment mechanism adapted to laterally engage an adjacent vertebral body and the attachment mechanism is substantially perpendicular to the sagittal plane of the spine.

17. The implant of claim 16 wherein the attachment mechanism is at least one keel.

18. An interspinous disk replacement implant having an articulation unit with a first end plate having a first inner surface with a first cylindrical socket therein, a second end plate having a second inner surface opposing the first inner surface, the second inner surface with a second cylindrical socket therein, and an articulation element, wherein the articulating element has four side walls and an upper convex cylindrical surface and a lower convex cylindrical surface oriented perpendicular to the upper convex cylindrical surface, wherein the upper convex cylindrical surface has an outer perimeter interfacing with all four side walls and the lower convex cylindrical surface has an outer perimeter interfacing with all four side walls, wherein the upper and lower convex cylindrical surfaces are at least partially received in the first and second cylindrical sockets, the improvement of the implant comprising an attachment mechanism extending from the articulating unit that is aligned with and supports the articulation element, the attachment mechanism adapted to laterally engage an adjacent vertebral body and the attachment mechanism is substantially perpendicular to the sagittal plane of the spine.

19. The implant of claim 18 wherein the attachment mechanism is at least one keel.

20. An intervertebral implant adapted to be inserted between adjacent vertebral bodies comprising:
- an articulating unit having a spacer within, wherein the spacer has four side walls and an upper convex cylindrical surface and a lower convex cylindrical surface oriented perpendicular to the upper convex cylindrical surface, wherein the upper convex cylindrical surface has an outer perimeter interfacing with all four side walls and the lower convex cylindrical surface has an outer perimeter interfacing with all four side walls, wherein the upper and the lower convex cylindrical surfaces are adapted to fit at least partially in the articulating unit and allow the articulating unit to pivot about the upper convex cylindrical surface in association with bending between flexion and extension, and about the lower convex cylindrical surface in association with lateral bending, the articulating unit further comprising:
  - an anterior end;
  - a posterior end;
  - a first lateral end; and
  - a second lateral end; and
- a keel extending from the articulating unit and oriented in a lengthwise direction between the first and second lateral ends.

21. The implant of claim 20 wherein the keel is configured to insert the implant between adjacent vertebral bodies from a lateral approach.

22. The implant of claim 20 wherein the keel further comprises at least one first keel extending from a first outer surface of the articulating unit.

23. The implant of claim 22 wherein the keel further comprises at least one second keel extending from a second outer surface of the articulating unit.

24. The implant of claim 20 wherein the keel includes a plurality of teeth angled in a desired direction.

25. The implant of claim 20 wherein the keel includes a plurality of teeth angled in a direction opposed to a desired direction of insertion into the vertebral body.

26. The implant of claim 20 wherein the keel further comprises a bore configured therethrough.

27. An intervertebral implant adapted to be inserted between adjacent vertebral bodies, the implant comprising:
- a first end plate having a first cylindrical cavity therein, the first end plate including a first keel protruding between a right lateral side and a left lateral side;
- a second end plate having a second cylindrical cavity therein, the second end plate including a second keel protruding between a right lateral side and a left lateral side; and
- a spacer, wherein the spacer has four side walls and an upper convex cylindrical surface and a lower convex cylindrical surface oriented perpendicular to the upper convex cylindrical surface, wherein the upper convex cylindrical surface has an outer perimeter interfacing with all four side walls and the lower convex cylindrical surface has an outer perimeter interfacing with all four side walls, wherein the upper and the lower convex cylindrical surfaces are in contact with the first cylindrical cavity and the second cylindrical cavity, the spacer configured to limit the first end plate between a first position and a second position in association with bending between flexion and extension, the spacer further configured to limit the second end plate between a third position and a fourth position in association with lateral bending, wherein the first and second positions are perpendicularly oriented to the third and fourth positions.

28. An intervertebral implant comprising:
- an articulating unit having an outer surface adapted to be substantially in contact with a vertebral body, wherein the articulating unit is configured to be inserted between adjacent vertebral bodies from a lateral approach and having an attachment mechanism that is substantially perpendicular to the sagittal plane of the spine; and
- a spacer positioned within the articulating unit, the spacer having four side walls, a first curved cylindrical surface and a second curved cylindrical surface oriented perpendicular to the first curved cylindrical surface, wherein the first curved cylindrical surface and the second curved cylindrical surface protrude outwards from the four sides away from a central point of the spacer, wherein the first curved cylindrical surface has an outer perimeter interfacing with all four side walls, wherein the second curved cylindrical surface has an outer perimeter interfacing with all four side walls, wherein the spacer allows the articulating unit to pivot about the first cylindrical surface in association with bending between flexion and extension, and about the second cylindrical surface in association with lateral bending.

29. An implant adapted to be inserted between adjacent vertebral bodies in a spine, the implant comprising:
- an articulating unit having an outer surface adapted to be substantially in contact with a vertebral body;
- a spacer positioned within the articulating unit and including four side walls, a first curved cylindrical surface and a second curved cylindrical surface oriented perpendicular to the first curved cylindrical surface, wherein the first curved cylindrical surface and the second curved cylindrical surface protrude outwards from all four sides away from a central point of the spacer, wherein the first curved cylindrical surface has an outer perimeter interfacing with all four side walls, wherein the second curved cylindrical surface has an outer perimeter interfacing with all four side walls, wherein the spacer allows the articulating unit to pivot about the first cylindrical surface in association with bending between flexion and extension, and about the second cylindrical surface in association with lateral bending; and
- a keel extending from the outer surface of the articulating unit and oriented to extend lengthwise between a first lateral end and a second lateral end of the unit.

30. An intervertebral implant comprising:
- an articulating unit adapted to be inserted between adjacent vertebral bodies, the articulating unit having a laterally configured keel adapted to mate with a vertebral body and the keel is substantially perpendicular to the sagittal plane of the spine; and
- a spacer within the articulating unit and having four walls and a first radial cylindrical surface and a second radial cylindrical surface oriented perpendicular to the first radial cylindrical surface, wherein the first radial cylindrical surface and the second radial cylindrical surface protrude outwards from all four side walls away from a central point of the spacer, wherein the first radial cylindrical surface has an outer perimeter interfacing with all four side walls, wherein the second radial cylindrical surface has an outer perimeter interfacing with all four side walls, wherein an upper portion of the articulating unit is capable of pivoting about the first cylindrical surface in association with flexion and extension, further wherein a lower portion of the articulating unit is capable of pivoting about the second cylindrical surface in association with lateral bending.

* * * * *